(12) United States Patent
Gross et al.

(10) Patent No.: US 10,675,248 B2
(45) Date of Patent: Jun. 9, 2020

(54) EXPANDABLE PILL

(71) Applicants: Yossi Gross, Moshav Mazor (IL); Oz Cabiri, Hod HaSharon (IL)

(72) Inventors: Yossi Gross, Moshav Mazor (IL); Oz Cabiri, Hod HaSharon (IL)

(73) Assignee: Alma Therapeutics Ltd., Petach Tikva (IL)

( * ) Notice: Subject to any disclaimer, the term of this patent is extended or adjusted under 35 U.S.C. 154(b) by 0 days.

(21) Appl. No.: 16/103,420

(22) Filed: Aug. 14, 2018

(65) Prior Publication Data
US 2020/0054568 A1    Feb. 20, 2020

(51) Int. Cl.
  *A61K 9/00*  (2006.01)
  *A61K 9/48*  (2006.01)
  *A61K 9/28*  (2006.01)

(52) U.S. Cl.
  CPC .......... *A61K 9/4808* (2013.01); *A61K 9/0053* (2013.01); *A61K 9/2866* (2013.01); *A61K 9/2873* (2013.01)

(58) Field of Classification Search
  CPC .................................................. A61K 9/0053
  See application file for complete search history.

(56) References Cited

U.S. PATENT DOCUMENTS

| | | | |
|---|---|---|---|
| 3,315,660 A | 4/1967 | Abella | |
| 4,425,117 A | 1/1984 | Hugemann et al. | |
| 4,507,115 A | 3/1985 | Kambara et al. | |
| 4,767,627 A | 8/1988 | Caldwell et al. | |
| 4,878,905 A | 11/1989 | Blass | |
| 5,002,772 A | 3/1991 | Curatolo et al. | |
| 5,090,963 A | 2/1992 | Gross et al. | |
| 5,167,626 A | 12/1992 | Casper et al. | |
| 5,170,801 A | 12/1992 | Casper et al. | |
| 5,217,449 A | 6/1993 | Yuda et al. | |
| 5,318,557 A | 6/1994 | Gross | |
| 5,425,706 A | 6/1995 | Gross et al. | |

(Continued)

FOREIGN PATENT DOCUMENTS

| | | |
|---|---|---|
| WO | 1996/037245 | 11/1996 |
| WO | 2004/066903 | 8/2004 |

(Continued)

OTHER PUBLICATIONS

Over Toorisaka et al (Acta Biomaterialia 8 (2012) 653-658). (Year: 2012).*

(Continued)

*Primary Examiner* — Benjamin J Packard
(74) *Attorney, Agent, or Firm* — Dekel Patent Ltd.; David Klein

(57) ABSTRACT

An ingestible pill is provided that includes an enteric coating and a medication-delivery device, which includes (a) a patch having upper and lower surfaces that face in generally opposite directions, and (b) needles. The patch is disposed within the enteric coating, folded so as to define one or more creases, which define respective inner and outer crease sides, wherein at least 50% of the needles are coupled to the patch along the inner crease sides. The patch is configured to assume, after the enteric coating dissolves, an expanded shape, in which the patch has an outer perimeter. Other embodiments are also described.

21 Claims, 17 Drawing Sheets

(56) References Cited

U.S. PATENT DOCUMENTS

| | | | |
|---|---|---|---|
| 5,443,843 A | 8/1995 | Curatolo et al. | |
| 5,443,846 A | 8/1995 | Yoshioka et al. | |
| 5,637,319 A | 6/1997 | Takada | |
| 5,814,020 A | 9/1998 | Gross | |
| 5,871,125 A | 2/1999 | Gross | |
| 5,951,538 A | 9/1999 | Joshi et al. | |
| 6,235,313 B1 | 5/2001 | Mathiowitz et al. | |
| 6,245,057 B1 | 6/2001 | Sieben et al. | |
| 6,632,216 B2 | 10/2003 | Houzego et al. | |
| 6,685,962 B2 | 2/2004 | Friedman et al. | |
| 6,830,560 B1 | 12/2004 | Gross et al. | |
| 6,958,034 B2 | 10/2005 | Iddan | |
| 6,994,095 B2 | 2/2006 | Burnett | |
| 7,009,634 B2 | 3/2006 | Iddan et al. | |
| 7,160,258 B2 | 1/2007 | Imran et al. | |
| 8,287,902 B2 | 10/2012 | Gross | |
| 8,295,932 B2 | 10/2012 | Bitton et al. | |
| 8,414,559 B2 | 4/2013 | Gross | |
| 8,764,733 B2 * | 7/2014 | Imran | A61K 9/0053 604/890.1 |
| 8,809,271 B2 | 8/2014 | Imran | |
| 8,846,040 B2 | 9/2014 | Imran | |
| 9,149,617 B2 | 10/2015 | Imran | |
| 9,402,807 B2 | 8/2016 | Imran | |
| 9,415,004 B2 | 8/2016 | Imran | |
| 9,492,396 B2 | 11/2016 | Gross | |
| 9,629,799 B2 | 4/2017 | Imran | |
| 9,757,548 B2 | 9/2017 | Imran | |
| 9,814,763 B2 | 11/2017 | Imran | |
| 9,844,505 B2 | 12/2017 | Imran | |
| 9,861,683 B2 | 1/2018 | Imran | |
| 10,029,080 B2 | 7/2018 | Imran | |
| 10,227,403 B2 | 3/2019 | Imran et al. | |
| 2002/0082543 A1 | 6/2002 | Park et al. | |
| 2003/0021845 A1 | 1/2003 | Friedman et al. | |
| 2003/0153866 A1 | 8/2003 | Long et al. | |
| 2004/0050394 A1 | 3/2004 | Jin | |
| 2004/0162469 A1 | 8/2004 | Imran | |
| 2004/0180086 A1 | 9/2004 | Ramtoola et al. | |
| 2004/0253304 A1 | 12/2004 | Gross et al. | |
| 2004/0267240 A1 | 12/2004 | Gross et al. | |
| 2005/0055039 A1 | 3/2005 | Burnett et al. | |
| 2005/0058701 A1 | 3/2005 | Gross et al. | |
| 2005/0125012 A1 * | 6/2005 | Houser | A61B 17/0057 606/148 |
| 2006/0045865 A1 | 3/2006 | Jacob et al. | |
| 2006/0142731 A1 | 6/2006 | Brooks | |
| 2006/0178557 A1 | 8/2006 | Mintchev et al. | |
| 2006/0276844 A1 | 12/2006 | Alon et al. | |
| 2007/0005147 A1 | 1/2007 | Levine et al. | |
| 2007/0156248 A1 | 7/2007 | Marco et al. | |
| 2007/0250132 A1 | 10/2007 | Burnett | |
| 2007/0293885 A1 | 12/2007 | Binmoeller | |
| 2008/0063703 A1 | 3/2008 | Gross et al. | |
| 2008/0188837 A1 | 8/2008 | Belsky et al. | |
| 2008/0234834 A1 | 9/2008 | Meade et al. | |
| 2008/0275430 A1 | 11/2008 | Belsky et al. | |
| 2009/0247992 A1 | 10/2009 | Shalon et al. | |
| 2010/0286628 A1 | 11/2010 | Gross | |
| 2011/0066175 A1 | 3/2011 | Gross | |
| 2011/0087195 A1 | 4/2011 | Uhland et al. | |
| 2013/0274659 A1 | 10/2013 | Imran et al. | |
| 2017/0066824 A1 | 3/2017 | Imran et al. | |
| 2018/0008771 A1 | 1/2018 | Imran et al. | |
| 2019/0060624 A1 | 2/2019 | Imran | |

FOREIGN PATENT DOCUMENTS

| | | |
|---|---|---|
| WO | 2005/105053 | 11/2005 |
| WO | 2007/007339 | 1/2007 |
| WO | 2007/086078 | 8/2007 |
| WO | 2008/023374 | 2/2008 |
| WO | 2008/121409 | 10/2008 |
| WO | 2008/121831 | 10/2008 |
| WO | 2008/154450 | 12/2008 |
| WO | 2010/128495 | 11/2010 |
| WO | 2011/151830 | 12/2011 |
| WO | 2013/003487 | 1/2013 |

OTHER PUBLICATIONS

Banerjee and Miragotri, "Intestinal patch systems for oral drug delivery", Current Opinion in Pharmacology 2017, 36:58-65 (Year: 2017).*

IntecPharma—Technology—The Accordion Pill (TM), downloaded May 21, 2018.

Klausner et al., "Expandable Gastroretentive Dosage Forms", Journal of Controlled Release 90 (2003) 143-162.

Medimetrics IntelliCap webpage, MediMetrics, downloaded Feb. 23, 2014.

Sarah L. Tao, et al., "Gastrointestinal patch systems for oral drug delivery", DDT vol. 10, No. 13, pp. 909-915. Jul. 2005.

Wen MM, "Advances and Challenges in the Dosage Form Design for the Treatment of Parkinson's Disease," Discovery Medicine, Dec. 24, 2012.

An Office Action dated Sep. 2, 2011, which issued during the prosecution of U.S. Appl. No. 12/508,086.

An Office Action dated Feb. 26, 2016, which issued during the prosecution of U.S. Appl. No. 14/319,808.

Notice of Allowance dated Jul. 15, 2016. which issued during the prosecution of U.S. Appl. No. 14/319,808.

* cited by examiner

EXPANDABLE PILL

FIELD OF THE INVENTION

The present invention generally relates to medical apparatus. Specifically, the present invention relates to an ingestible capsule for administering medication to a subject.

BACKGROUND OF THE INVENTION

Medication is frequently stored in a capsule and administered to a subject who swallows the capsule. The medication passes through the intestinal wall and enters the blood of the subject.

U.S. Pat. No. 8,287,902 to Gross, which is incorporated herein by reference, describes an ingestible capsule for delivering medication to a subject. A capsule coating dissolves in a gastrointestinal tract of the subject. An inner core of the capsule has an outer surface associated therewith. The outer surface is disposed within the coating and expands when the coating dissolves. A medication is disposed on the outer surface, and the outer surface is configured such that the medication contacts an intestinal wall of the subject when the outer surface expands.

U.S. Pat. No. 9,492,396 to Gross, which is incorporated herein by reference, describes an ingestible pill includes a coating configured to dissolve in a small intestine; a core, which includes a medication-delivery element, which (a) has a compressed shape when disposed within the coating, and (b) is configured to assume, after the coating dissolves, an expanded shape; a medication; and a mucoadhesive. When unconstrained in the expanded shape, the medication-delivery element (a) is shaped so as to define first and second surfaces on opposite sides of the medication-delivery element, which have respective outer perimeters, which surround respective spaces of the respective surfaces, which spaces have respective greatest dimensions equal to between 2 and 10 cm, and each of which spaces has an area equal to at least 50% of the square of the greatest dimension; and (b) has an average thickness between the first and the second surfaces of less than 6 mm. Each of the medication and the mucoadhesive at least partially coats the first surface.

SUMMARY OF APPLICATIONS

In some applications of the present invention, an ingestible pill is provided that comprises an enteric coating; and a medication-delivery device, which (a) is pliable, (b) is disposed within the enteric coating, having a compressed shape enabled by the pliability, and (c) is shaped so as to define (i) one or more medication chambers and (ii) one or more expansible chambers. The medication-delivery device further comprises (i) one or more outer surfaces, all of which are pliable; (ii) hollow medication-delivery needles, which are coupled to at least one of the one or more outer surfaces; and (iii) a medication, which is contained within the one or more medication chambers. The medication-delivery device is configured to assume, after the enteric coating dissolves, an expanded shape in which the hollow medication-delivery needles (a) are in fluid communication with the one or more medication chambers and (b) extend away from the medication-delivery device. The medication-delivery device is configured such that expansion of the one or more expansible chambers forces the medication from the one or more medication chambers and out of the medication-delivery device through the hollow medication-delivery needles.

There is therefore provided, in accordance with an application of the present invention, apparatus including an ingestible pill, which includes:

an enteric coating; and a medication-delivery device, which includes (a) a patch having upper and lower surfaces that face in generally opposite directions; and (b) needles, wherein the patch is disposed within the enteric coating, folded so as to define one or more creases, which define respective inner and outer crease sides, wherein at least 50% of the needles are coupled to the patch along the inner crease sides, and wherein the patch is configured to assume, after the enteric coating dissolves, an expanded shape, in which the patch has an outer perimeter.

For some applications, the patch can inscribe a circle having a diameter of between 2 and 10 cm when the patch assumes the expanded shape and is unconstrained.

For some applications, each of the needles has a length of between 20 and 300 microns.

For some applications, the patch is configured such that the expanded shape is generally flat when the medication-delivery device is unconstrained.

For some applications, a greatest radius of the needles is between 20 and 150 microns.

For some applications, the patch is annular.

For some applications, between 0% and 10% of the needles are coupled to the patch along the outer crease sides when the patch is disposed within the enteric coating.

For some applications, the ingestible pill is configured such that when the patch assumes the expanded shape upon dissolving of the enteric coating in a small intestine of a subject, the upper surface of the patch contacts an intestinal wall, thereby bringing the needles into contact with the intestinal wall.

For some applications, at least 50% of the needles are coupled to the upper surface of the patch along the inner crease sides when the patch is disposed within the enteric coating.

For some applications, at least 80% of the needles are coupled to the upper surface of the patch when the patch is disposed within the enteric coating.

For some applications, the patch is disposed within the enteric coating, folded such that when the patch assumes the expanded shape upon dissolving of the enteric coating in the small intestine, the upper face of the patch contacts the intestinal wall, thereby bringing the needles into contact with the intestinal wall.

For some applications, the medication-delivery device further includes a medication, and the needles are configured to deliver the medication.

For some applications, the needles are hollow and are configured to deliver the medication.

For some applications, the needles include a solid medication.

For some applications, the patch is disposed within the enteric coating, folded so as to define a plurality of creases.

For some applications, the patch is disposed within the enteric coating, folded first in half and then accordion-folded.

For some applications, the needles are not coupled to respective inner crease sides of a portion of the creases.

For some applications, the needles are not coupled to respective inner crease sides of two or more of the creases.

There is further provided, in accordance with an application of the present invention, apparatus including an ingestible pill, which includes:

an enteric coating; and
a medication-delivery device, which includes:
(a) a patch, which (i) has upper and lower surfaces that face in generally opposite directions, (ii) has a compressed shape when disposed within the enteric coating, (iii) is shaped so as to define an outer perimeter, and (iv) includes at least first and second layers, which are arranged so as to define one or more expansible chambers between the first layer and the second layer, wherein the first layer and the second layer are fixed together at fixation locations, wherein some of the fixation locations are located at or near the outer perimeter and some of the fixation locations are located at least 2 mm from the outer perimeter; and
(b) needles, which are coupled to the upper surface at respective needle locations,
wherein the patch is configured such that, if the patch were laid generally flat on a flat horizontal surface, at least 80% of the needle locations would be horizontally offset from the fixation locations, and
wherein the patch is configured to assume an expanded shape after the enteric coating dissolves.

For some applications, the patch can inscribe a circle having a diameter of between 2 and 10 cm when the patch assumes the expanded shape and is unconstrained.

For some applications, each of the needles has a length of between 20 and 300 microns.

For some applications, the patch is configured such that, if the patch were laid generally flat on the flat horizontal surface, all of the needle locations would be horizontally offset from the fixation locations.

For some applications, the patch is configured such that, if the patch were laid generally flat on the flat horizontal surface, each of the needle locations would be located at least 1 mm horizontally from a nearest one of the fixation locations.

For some applications, the patch is configured such that, if the patch were laid generally flat on the flat horizontal surface, each of the needle locations would be located approximately horizontally centered between a nearest two of the fixation locations.

For some applications, the patch is configured such that the expanded shape is generally flat when the medication-delivery device is unconstrained.

For some applications, the needles include a solid medication.

For some applications, at least some of the fixation locations are arranged in a plurality of points.

For some applications, the patch is annular.

For some applications, the patch is configured such that, if the patch were laid generally flat on the flat horizontal surface, the needle locations would be located on average at least 1 mm from respective nearest fixation locations.

For some applications, the patch is configured such that, if the patch were laid generally flat on the flat horizontal surface, the needle locations would be located on average at least 2 mm horizontally from respective nearest fixation locations.

For some applications, the medication-delivery device further includes a medication, and the needles are configured to deliver the medication.

For some applications, wherein the patch further includes a third layer, which defines the upper surface, wherein the second layer and the third layer are arranged so as define one or more medication chambers between the second layer and the third layer, wherein the one or more medication chambers contain the medication, and wherein the needles are hollow.

For some applications, the medication is contained within the one or more expansible chambers, and the needles are (a) hollow, (b) coupled to the second layer in fluid communication with the one or more expansible chambers, when the patch assumes the expanded shape, and (c) configured to deliver the medication.

For some applications, the ingestible pill is configured such that when the patch assumes the expanded shape upon dissolving of the enteric coating in a small intestine of a subject, the upper surface of the patch contacts an intestinal wall, thereby bringing the needles into contact with the intestinal wall.

For some applications, at least some of the fixation locations are arranged in a plurality of segments.

For some applications, at least some of the segments are curved when the patch assumes the expanded shape.

For some applications, at least some of the curved segments are arranged equidistantly around a center point of the patch when the patch assumes the expanded shape.

For some applications, the one or more expansible chambers include one or more inflatable chambers.

For some applications, the one or more inflatable chambers contain a substance that produces gas upon contact with liquid.

For some applications, the one or more expansible chambers contain a substance that expands upon contact with liquid.

For some applications, the substance includes a polymer.

For some applications, the first layer is liquid-permeable and substantially not gas-permeable.

For some applications, the first layer includes biocellulose.

For some applications, the patch is disposed within the enteric coating, folded so as to define one or more creases, which define respective inner and outer crease sides, and at least 50% of the needles are coupled to the upper surface of the patch along the inner crease sides.

For some applications, the patch is disposed within the enteric coating, folded so as to define a plurality of creases.

For some applications, the needles are not coupled to respective inner crease sides of a portion of the creases.

For some applications, between 0% and 10% of the needles are coupled to the patch along the outer crease sides when the patch is disposed within the enteric coating.

There is still further provided, in accordance with an application of the present invention, apparatus including an ingestible pill, which includes:
an enteric coating; and
a medication-delivery device, which (a) is pliable, (b) is disposed within the enteric coating, having a compressed shape enabled by the pliability, (c) is shaped so as to define (i) one or more medication chambers and (ii) one or more expansible chambers, and (d) includes:
(i) one or more outer surfaces, all of which are pliable;
(ii) hollow medication-delivery needles, which are coupled to at least one of the one or more outer surfaces; and
(iii) a medication, which is contained within the one or more medication chambers,
wherein the medication-delivery device is configured to assume, after the enteric coating dissolves, an expanded shape in which the hollow medication-delivery needles (a)

are in fluid communication with the one or more medication chambers and (b) extend away from the medication-delivery device, and wherein the medication-delivery device is configured such that expansion of the one or more expansible chambers forces the medication from the one or more medication chambers and out of the medication-delivery device through the hollow medication-delivery needles.

For some applications, the medication-delivery device is shaped as a patch.

For some applications, the medication-delivery device is shaped as a circular or elliptical torus.

For some applications, the one or more expansible chambers include one or more inflatable chambers.

For some applications, the one or more inflatable chambers contain a substance that produces gas upon contact with liquid.

For some applications, at least one of the one or more outer surfaces includes biocellulose.

There is additionally provided, in accordance with an application of the present invention, apparatus including an ingestible pill which includes:
an enteric coating; and
a medication-delivery device, which (a) has a compressed shape when disposed within the enteric coating, (b) is shaped so as to define (i) one or more medication chambers and (ii) one or more inflatable chambers, and (c) includes:
 (i) one or more outer surfaces, at least one of which includes biocellulose;
 (ii) a substance, which is contained within the one or more inflatable chambers, and which produces gas upon contact with liquid;
 (iii) hollow medication-delivery needles, which are coupled to at least one of the one or more outer surfaces; and
 (iv) a medication, which is contained within the one or more medication chambers,
wherein the medication-delivery device is configured to assume, after the enteric coating dissolves, an expanded shape in which the hollow medication-delivery needles (a) are in fluid communication with the one or more medication chambers and (b) extend away from the medication-delivery device, and
wherein the medication-delivery device is configured such that inflation of the one or more inflatable chambers forces the medication from the one or more medication chambers and out of the medication-delivery device through the hollow medication-delivery needles.

There is yet additionally provided, in accordance with an application of the present invention, apparatus including an ingestible pill, which includes:
an enteric coating; and
a medication-delivery device, which includes:
 (a) a patch, which has a compressed shape when disposed within the enteric coating, and which is shaped so as to define an outer perimeter, and which includes at least first, second, and third layers, which are arranged so as to define:
  (i) one or more medication chambers between the second layer and the third layer, and
  (ii) one or more expansible chambers between the first layer and the second layer, wherein the first layer and the second layer are fixed together at fixation locations, wherein some of the fixation locations are located at or near the outer perimeter and some of the fixation locations are located at least 2 mm from the outer perimeter; and
 (b) a medication, which is contained within the one or more medication chambers,
wherein the patch is configured to assume, after the enteric coating dissolves, an expanded shape, and
wherein the third layer is permeable to the medication, such that expansion of the one or more expansible chambers forces the medication from the one or more medication chambers, through the third layer, and out of the medication-delivery device.

For some applications, the patch can inscribe a circle having a diameter of between 2 and 10 cm when the patch assumes the expanded shape and is unconstrained.

For some applications, the patch is configured such that the expanded shape is generally flat when the medication-delivery device is unconstrained.

For some applications, the at least some of the fixation locations are arranged in a plurality of points.

For some applications, the third layer is shaped so as to define one or more pores that provide the permeability.

For some applications, the patch is annular.

For some applications, the medication-delivery device includes a plurality of hollow medication-delivery needles, which are coupled to the third layer, and which, when the patch assumes the expanded shape, are in fluid communication with the one or more medication chambers and extend away from the patch.

For some applications, the ingestible pill is configured such that when the patch assumes the expanded shape upon dissolving of the enteric coating in a small intestine of a subject, the third layer of the patch contacts an intestinal wall, thereby bringing the hollow medication-delivery needles into contact with the intestinal wall.

For some applications, the patch is disposed within the enteric coating, folded so as to define one or more creases, which define respective inner and outer crease sides, and at least 50% of the hollow medication-delivery needles are coupled to the third layer of the patch along the inner crease sides.

For some applications, the patch is disposed within the enteric coating, folded so as to define a plurality of creases.

For some applications, the hollow medication-delivery needles are not coupled to respective inner crease sides of a portion of the creases.

For some applications, between 0% and 10% of the hollow medication-delivery needles are coupled to the patch along the outer crease sides when the patch is disposed within the enteric coating.

For some applications, the at least some of the fixation locations are arranged in a plurality of segments.

For some applications, at least some of the segments are curved when the patch assumes the expanded shape.

For some applications, at least some of the curved segments are arranged equidistantly around a center point of the patch when the patch assumes the expanded shape.

For some applications, the one or more expansible chambers include one or more inflatable chambers.

For some applications, the one or more inflatable chambers contain a substance that produces gas upon contact with liquid.

For some applications, the one or more expansible chambers contain a substance that expands upon contact with liquid.

For some applications, the substance includes a polymer.

For some applications, the first layer is liquid-permeable and substantially not gas-permeable.

For some applications, the first layer includes biocellulose.

There is also provided, in accordance with an application of the present invention, apparatus including an ingestible pill, which includes:
an enteric coating; and
a medication-delivery device, which includes:
(a) a patch, which has a compressed shape when disposed within the enteric coating, and which is shaped so as to define an outer perimeter, and which includes at least first, second, third, and fourth layers, which are arranged so as to define:
(i) one or more medication chambers between the third layer and the fourth layer,
(ii) one or more first expansible chambers between the second and the third layers, and
(iii) one or more second expansible chambers between the first layer and the second layer, wherein the first layer and the second layer are fixed together at fixation locations, wherein some of the fixation locations are located at or near the outer perimeter and some of the fixation locations are located at least 2 mm from the outer perimeter; and
(b) a medication, which is contained within the one or more medication chambers,
wherein the patch is configured to assume, after the enteric coating dissolves, an expanded shape, and
wherein the fourth layer is permeable to the medication, such that expansion of the one or more second expansible chambers forces the medication from the one or more medication chambers, through the fourth layer, and out of the medication-delivery device.

For some applications, the patch can inscribe a circle having a diameter of between 2 and 10 cm when the patch assumes the expanded shape and is unconstrained.

For some applications, the patch is configured such that the expanded shape is generally flat when the medication-delivery device is unconstrained.

For some applications, at least some of the fixation locations are arranged in a plurality of points.

For some applications, the medication-delivery device is configured such that upon contact with liquid, the one or more second expansible chambers begin to expand before the one or more first expansible chambers begin to expand.

For some applications, the fourth layer is shaped so as to define one or more pores that provide the permeability.

For some applications, the patch is annular.

For some applications, the medication-delivery device includes a plurality of hollow medication-delivery needles, which are coupled to the fourth layer, and, which, when the patch assumes the expanded shape, are in fluid communication with the one or more medication chambers and extend away from the patch.

For some applications, the ingestible pill is configured such that when the patch assumes the expanded shape upon dissolving of the enteric coating in a small intestine of a subject, the fourth layer of the patch contacts an intestinal wall, thereby bringing the hollow medication-delivery needles into contact with the intestinal wall.

For some applications, the patch is disposed within the enteric coating, folded so as to define one or more creases, which define respective inner and outer crease sides, and at least 50% of the hollow medication-delivery needles are coupled to the fourth layer of the patch along the inner crease sides.

For some applications, the patch is disposed within the enteric coating, folded so as to define a plurality of creases.

For some applications, the hollow medication-delivery needles are not coupled to respective inner crease sides of a portion of the creases.

For some applications, between 0% and 10% of the hollow medication-delivery needles are coupled to the patch along the outer crease sides when the patch is disposed within the enteric coating.

For some applications, at least some of the fixation locations are arranged in a plurality of segments.

For some applications, at least some of the segments are curved when the patch assumes the expanded shape.

For some applications, at least some of the curved segments are arranged equidistantly around a center point of the patch when the patch assumes the expanded shape.

For some applications, the one or more second expansible chambers include one or more inflatable chambers.

For some applications, the one or more second inflatable chambers contain a substance that produces gas upon contact with liquid.

For some applications:
the one or more first expansible chambers include one or more first inflatable chambers, and
the second layer is gas-permeable, such that upon inflation of the one or more second inflatable chambers, gas passes from the one or more second inflatable chambers through the gas-permeable second layer to the one or more first inflatable chambers, such that the one or more second inflatable chambers begin to inflate before the one or more first inflatable chambers begin to inflate.

For some applications, the second layer is shaped so as define a plurality of pores that provides the gas-permeability.

For some applications, the second layer is configured to tear upon inflation of the one or more second inflatable chambers, thereby providing the gas-permeability.

For some applications, the one or more second expansible chambers contain a substance that expands upon contact with liquid.

For some applications, the substance includes a polymer.

For some applications, the first layer is liquid-permeable and substantially not gas-permeable.

For some applications, the first layer includes biocellulose.

For some applications, the second layer is liquid-permeable and substantially not gas-permeable.

For some applications, the first layer includes biocellulose.

There is further provided, in accordance with an application of the present invention, apparatus including an ingestible pill, which includes:
an enteric coating; and
a medication-delivery device, which has a compressed shape when disposed within the enteric coating, and includes:
a patch having upper and lower surfaces that face in generally opposite directions, wherein the patch includes a non-metal material; and
one or more elastic struts, which are fixed to the patch,
wherein the one or more elastic struts are configured, upon the enteric coating dissolving, to transition the medication-delivery device from the compressed shape to an expanded shape, in which the patch has an outer perimeter.

For some applications, the patch can inscribe a circle having a diameter of between 2 and 10 cm when the patch assumes the expanded shape and is unconstrained.

For some applications, the patch is elliptical or circular.

For some applications, the medication-delivery device further includes a medication.

For some applications, at least 75% of the medication adheres to the upper surface of the patch when the medication-delivery device is disposed in the enteric coating.

For some applications, the patch is configured such that the expanded shape is generally flat when the medication-delivery device is unconstrained.

For some applications, the patch is annular.

For some applications, the one or more elastic struts include metal.

For some applications, the one or more elastic struts include a shape memory alloy.

For some applications, the one or more elastic struts include stainless steel.

There is still further provided, in accordance with an application of the present invention, a method including:

receiving, by a subject, an ingestible pill, which includes (i) an enteric coating and (ii) a medication-delivery device, which includes (a) a patch having upper and lower surfaces that face in generally opposite directions, and needles, wherein the patch is disposed within the enteric coating, folded so as to define one or more creases, which define respective inner and outer crease sides, wherein at least 50% of the needles are coupled to the patch along the inner crease sides; and swallowing the ingestible pill by the subject, so that the coating dissolves in the small intestine and the patch assumes an expanded shape, in which the patch has an outer perimeter.

For some applications, between 0% and 10% of the needles are coupled to the patch along the outer crease sides when the patch is disposed within the enteric coating.

For some applications:

the ingestible pill is configured such that when the patch assumes the expanded shape upon dissolving of the enteric coating in a small intestine of a subject, the upper surface of the patch contacts an intestinal wall, thereby bringing the needles into contact with the intestinal wall, and at least 50% of the needles are coupled to the upper surface of the patch along the inner crease sides when the patch is disposed within the enteric coating.

For some applications, the medication-delivery device further includes a medication, and the needles are configured to deliver the medication.

For some applications, the needles include a solid medication.

For some applications, the patch is disposed within the enteric coating, folded so as to define a plurality of creases, and the needles are not coupled to respective inner crease sides of a portion of the creases.

There is additionally provided, in accordance with an application of the present invention, a method including:

receiving, by a subject, an ingestible pill, which includes (i) an enteric coating and (ii) a medication-delivery device, which includes (a) a patch, which (A) has upper and lower surfaces that face in generally opposite directions, (B) has a compressed shape when disposed within the enteric coating, (C) is shaped so as to define an outer perimeter, and (D) includes at least first and second layers, which are arranged so as to define one or more expansible chambers between the first layer and the second layer, wherein the first layer and the second layer are fixed together at fixation locations, wherein some of the fixation locations are located at or near the outer perimeter and some of the fixation locations are located at least 2 mm from the outer perimeter, and (b) needles, which are coupled to the upper surface at respective needle locations, wherein the patch is configured such that, if the patch were laid generally flat on a flat horizontal surface, at least 80% of the needle locations would be horizontally offset from the fixation locations; and swallowing the ingestible pill by the subject, so that the coating dissolves in the small intestine and the patch assumes an expanded shape.

There is yet additionally provided, in accordance with an application of the present invention, a method including:

receiving, by a subject, an ingestible pill, which includes (i) an enteric coating and (ii) a medication-delivery device, which (a) is pliable, (b) is disposed within the enteric coating, having a compressed shape enabled by the pliability, (c) is shaped so as to define (A) one or more medication chambers and (B) one or more expansible chambers, and (d) includes (A) one or more outer surfaces, all of which are pliable, (B) hollow medication-delivery needles, which are coupled to at least one of the one or more outer surfaces, and (C) a medication, which is contained within the one or more medication chambers; and swallowing the ingestible pill by the subject, so that the coating dissolves in the small intestine and the medication-delivery device assumes an expanded shape in which the hollow medication-delivery needles (a) are in fluid communication with the one or more medication chambers and (b) extend away from the medication-delivery device, wherein the medication-delivery device is configured such that expansion of the one or more expansible chambers forces the medication from the one or more medication chambers and out of the medication-delivery device through the hollow medication-delivery needles.

There is also provided, in accordance with an application of the present invention, a method including:

receiving, by a subject, an ingestible pill, which includes (i) an enteric coating and (ii) a medication-delivery device, which (a) has a compressed shape when disposed within the enteric coating, (b) is shaped so as to define (A) one or more medication chambers and (B) one or more inflatable chambers, and (c) includes (A) one or more outer surfaces, at least one of which includes biocellulose, (B) a substance, which is contained within the one or more inflatable chambers, and which produces gas upon contact with liquid, (C) hollow medication-delivery needles, which are coupled to at least one of the one or more outer surfaces, and (D) a medication, which is contained within the one or more medication chambers; and swallowing the ingestible pill by the subject, so that the coating dissolves in the small intestine and the medication-delivery device assumes an expanded shape an expanded shape in which the hollow medication-delivery needles (a) are in fluid communication with the one or more medication chambers and (b) extend away from the medication-delivery device, wherein the medication-delivery device is configured such that inflation of the one or more inflatable chambers forces the medication from the one or more medication chambers and out of the medication-delivery device through the hollow medication-delivery needles.

There is further provided, in accordance with an application of the present invention, a method including:

receiving, by a subject, an ingestible pill, which includes (i) an enteric coating and (ii) a medication-delivery device, which includes (a) a patch, which has a compressed shape when disposed within the enteric coating, and which is shaped so as to define an outer perimeter, and which includes at least first, second, and third layers, which are arranged so as to define (A) one or more medication chambers between the second layer and the third layer, and (B) one or more expansible chambers between the first layer and the second layer, wherein the first layer and the second layer are fixed together at fixation locations, wherein some of the fixation locations are located at or near the outer perimeter and some of the fixation locations are located at least 2 mm from the outer perimeter, and (b) a medication, which is contained within the one or more medication chambers; and swallowing the ingestible pill by the subject, so that the coating dissolves in the small intestine and the patch assumes an expanded shape, wherein the third layer is permeable to the medication, such that expansion of the one or more expansible chambers forces the medication from the one or more medication chambers, through the third layer, and out of the medication-delivery device.

There is still further provided, in accordance with an application of the present invention, a method including:

receiving, by a subject, an ingestible pill, which includes (i) an enteric coating and (ii) a medication-delivery device, which includes (a) a patch, which has a compressed shape when disposed within the enteric coating, and which is shaped so as to define an outer perimeter, and which includes at least first, second, third, and fourth layers, which are arranged so as to define (A) one or more medication chambers between the third layer and the fourth layer, (B) one or more first expansible chambers between the second and the third layers, and (C) one or more second expansible chambers between the first layer and the second layer, wherein the first layer and the second layer are fixed together at fixation locations, wherein some of the fixation locations are located at or near the outer perimeter and some of the fixation locations are located at least 2 mm from the outer perimeter, and (b) a medication, which is contained within the one or more medication chambers; and swallowing the ingestible pill by the subject, so that the coating dissolves in the small intestine and the patch assumes an expanded shape, wherein the fourth layer is permeable to the medication, such that expansion of the one or more second expansible chambers forces the medication from the one or more medication chambers, through the fourth layer, and out of the medication-delivery device.

There is additionally provided, in accordance with an application of the present invention, a method including:

receiving, by a subject, an ingestible pill, which includes (i) an enteric coating and (ii) a medication-delivery device, which has a compressed shape when disposed within the enteric coating, and includes (a) a patch having upper and lower surfaces that face in generally opposite directions, wherein the patch includes a non-metal material, and (b) one or more elastic struts, which are fixed to the patch; and swallowing the ingestible pill by the subject, so that the coating dissolves in the small intestine and the one or more elastic struts transition the medication-delivery device from the compressed shape to an expanded shape, in which the patch has an outer perimeter.

The present invention will be more fully understood from the following detailed description of embodiments thereof, taken together with the drawings, in which:

DETAILED DESCRIPTION OF EMBODIMENTS

Figure 1A:
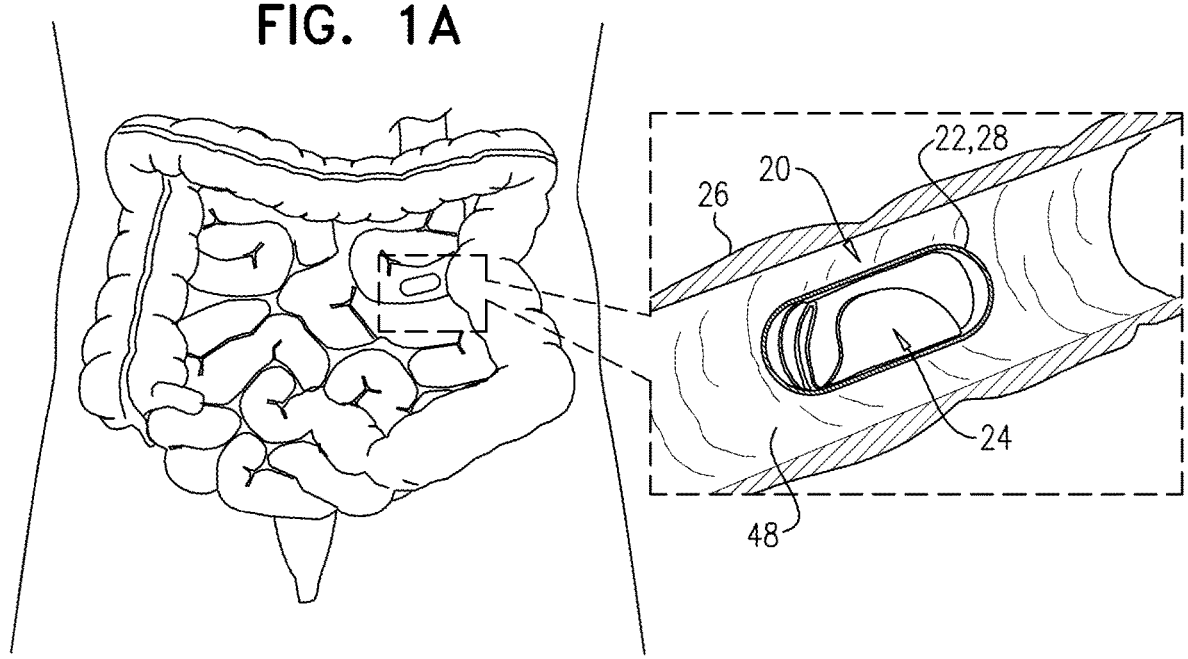
FIGS. 1A-B are schematic illustrations of an ingestible pill, for ingestion by a subject, in accordance with an application of the present invention.
Figure 1B:
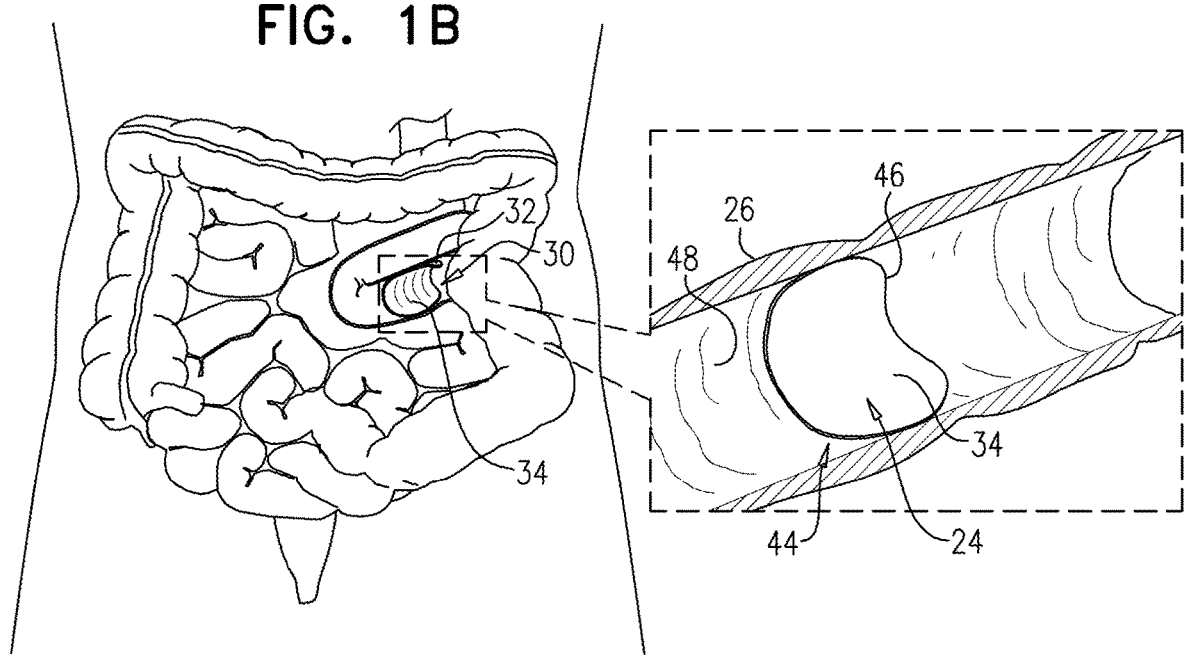

FIGS. 1A-B are schematic illustrations of an ingestible pill 20, for ingestion by a subject, in accordance with an application of the present invention. Ingestible pill 20 comprises an enteric coating 22 and a medication-delivery device 24.

Enteric coating 22 is configured to dissolve in a small intestine 26 (e.g., a duodenum, jejunum, and/or ileum) of the subject. Typically, enteric coating 22 is pH-sensitive, and may be configured to dissolve within 10 minutes (e.g., within 5 minutes) within a range of pH values, which range has a low end of between 6.5 and 8.5 (and, optionally, a high end of between 7.5 and 14, such as between 7.5 and 9.5). For example, enteric coating 22 may comprise gelatin. For some applications, as shown in FIG. 1A, pill 20 comprises a shell 28, which comprises enteric coating 22. Alternatively, for some applications, medication-delivery device 24 is directly coated with enteric coating 22 (configuration not shown). Typically, pill 20 has a length of at least 5 mm, no more than 30 mm, and/or between 5 and 30 mm before the enteric coating dissolves.

Medication-delivery device 24 comprises (a) a patch 30 having an upper (intestinal-wall-contact) surface 32 and a lower (intestinal-lumen-facing) surface 34, which face in generally opposite directions, and (b) needles 40. Medication-delivery device 24 (a) has a compressed shape 42 when disposed within coating 22, as shown in FIG. 1A, and (b) is configured to assume, after enteric coating 22 dissolves, an expanded shape 44, in which patch 30 has an outer perimeter 46. FIG. 1B shows medication-delivery device 24 in expanded shape 44, constrained by a wall 48 of small intestine 26. Typically, patch 30 comprises a non-metal material, such as an elastic material (e.g., polyurethane or silicone), or alternatively a shape memory material such as Nitinol, which, for example, may be set to change into a super-elastic condition after reaching a temperature of 32-34 degrees C. Medication-delivery device 24 expands, such as by stretching, unfolding, and/or unrolling, in response to no longer being constrained by enteric coating 22, and/or in response to contact of medication-delivery device 24 with fluid in small intestine 26.

Typically, each of needles 40 has a length of at least 20 microns (e.g., at least 50 microns), no more than 300 microns (e.g., no more than 250 microns), and/or between 20 and 300 microns, such as between 50 and 250 microns. Typically, a greatest dimension of needles 40, measured perpendicular to a long axis, is between 40 and 300 microns. For some applications, needles 40 are conical or pyramidal, and the greatest dimension is thus at the bases of the cones or pyramids of the needles.

For some applications, medication-delivery device 24 is biodegradable in small intestine 26. For some applications, patch 30 comprises an elastomer, such as polyethylene or silicone.

For some applications, such as shown in FIGS. 1A-B and described hereinbelow with reference to FIGS. 2A-F, 3A-B, 4A-F, 5A-B, and 6A-F, needles 40 are medication-needles 50, which comprise a solid medication (for example, the solid medication may be integrated in a glucose structure). For other applications, such as described hereinbelow with reference to FIGS. 7A-C, 8A-B, 9A-B, and 10A-B, medication-delivery device 24 further comprises a medication 52 (e.g., a liquid medication), and needles 40 are medication-delivery needles 54, which are configured to deliver medication 52. For these applications, medication-delivery needles 54 are typically hollow and are configured to deliver medication 52.

Typically, patch 30 is configured such that expanded shape 44 is generally flat when medication-delivery device 24 is unconstrained, such as shown in FIGS. 2A, 3A, 4A, 5A, and 6A, and assumes a curved shape when constrained by wall 48 of small intestine 26, such as shown in FIG. 1B. Ingestible pill 20 is configured such that when patch 30 assumes expanded shape 44 upon dissolving of enteric coating 22 in small intestine 26, upper surface 32 of patch 30 contacts intestinal wall 48, thereby bringing needles 40 into contact with intestinal wall 48. Typically, but not necessarily, needles 40 penetrate intestinal wall 48, typically the villi thereof, in order to enhance uptake of the medication. In addition, needles 40 may also serve as temporary anchors that hold patch 30 in place during medication delivery. Medication-delivery device 24 typically remains axially stationary in the small intestine long enough for needles 40 to slowly push into tissue of intestinal wall 48, such as because of peristalsis, and to inject medication, for applications in which the needles are hollow, or to dissolve, for applications in which the needles comprise medication. For some applications in which medication-delivery device 24 expands (e.g., inflates), the expansion itself does not generally push the needles into the intestinal wall. Following delivery of the medication, medication-delivery device 24 is passed from the body.

Once expanded, upper surface 32 of patch 30 establishes good (complete or nearly complete) contact with intestinal wall 48, as shown in FIG. 1B. The shape and dimensions of medication-delivery device 24 may contribute to this good contact by preventing other, lower-contact-level orientations of the patch in the lumen of small intestine 26. The location of patch 30 is generally unaffected by peristalsis, and does not block food passing through the intestine.

For some applications, medication-delivery device 24 further comprises a mucoadhesive that at least partially coats upper surface 32. For example, the mucoadhesive may be sprayed or printed on upper surface 32 using techniques known in the art. The mucoadhesive transiently helps adhere upper surface 32 in position against intestinal wall 48 during delivery of the medication through intestinal wall 48. For example, the mucoadhesive may include an adhesive agent described in U.S. Pat. No. 6,235,313 to Mathiowitz et al., or in an article by Tao et al., Tao et al., entitled, "Gastrointestinal patch systems for oral drug delivery," Drug Discovery Today, Vol. 10(13), July 2005, both of which references are incorporated herein by reference.

Figure 2A:
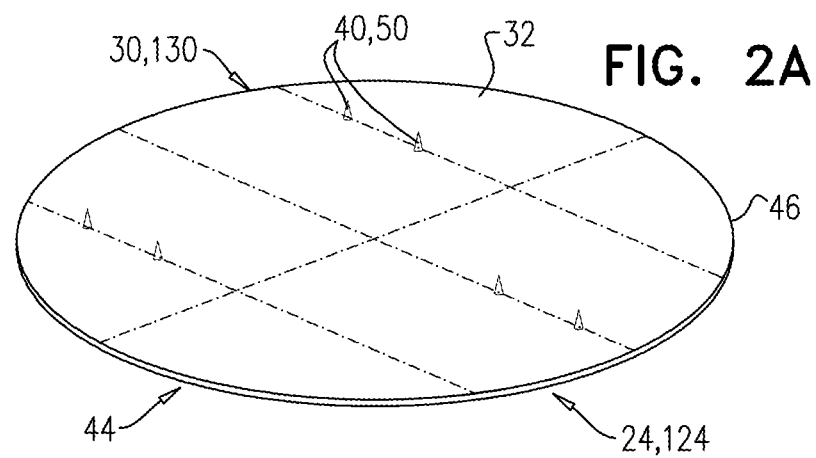
FIGS. 2A-F are schematic illustrations of a medication-delivery device of an ingestible pill, in accordance with an application of the present invention.
Figure 2B:
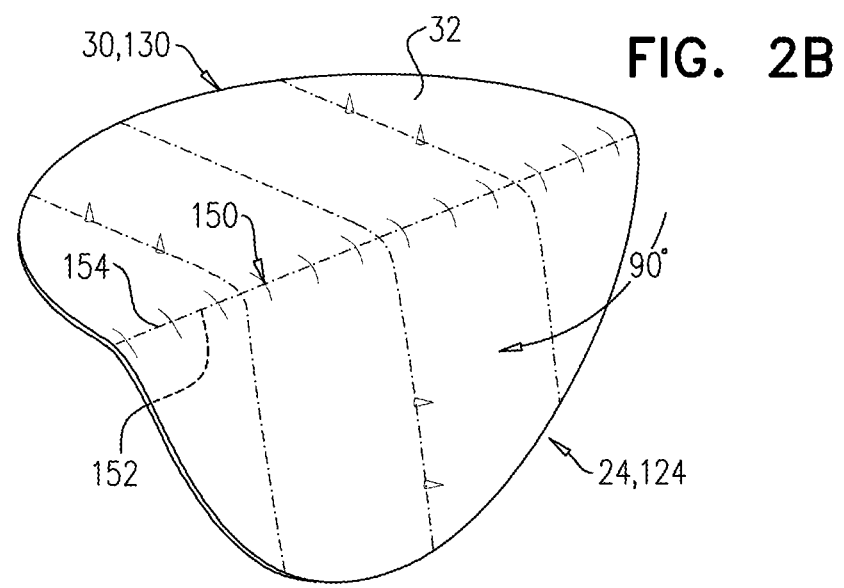
Figure 2C:
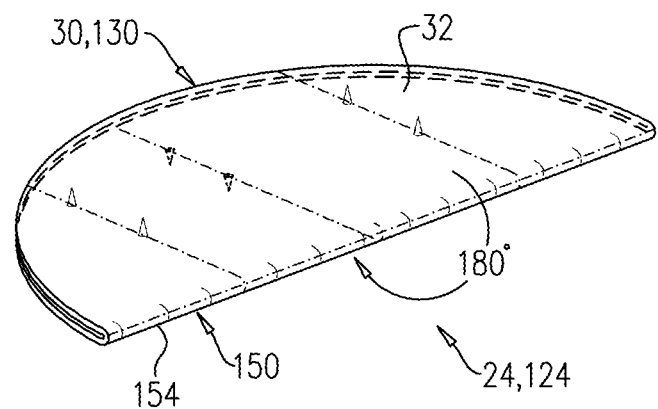
Figure 2D:
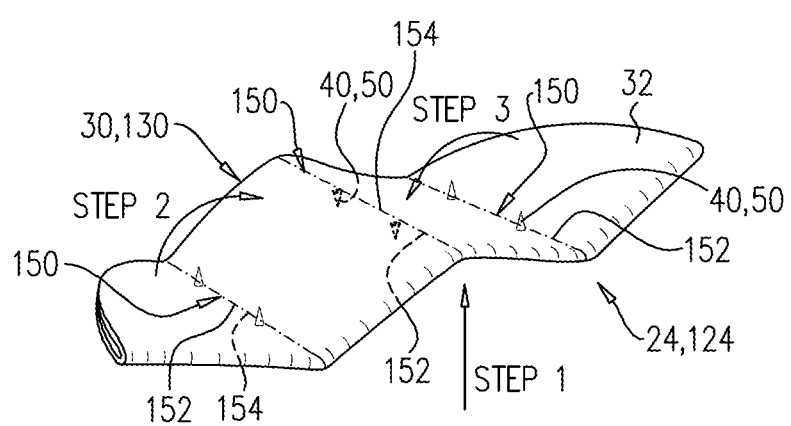
Figure 2E:
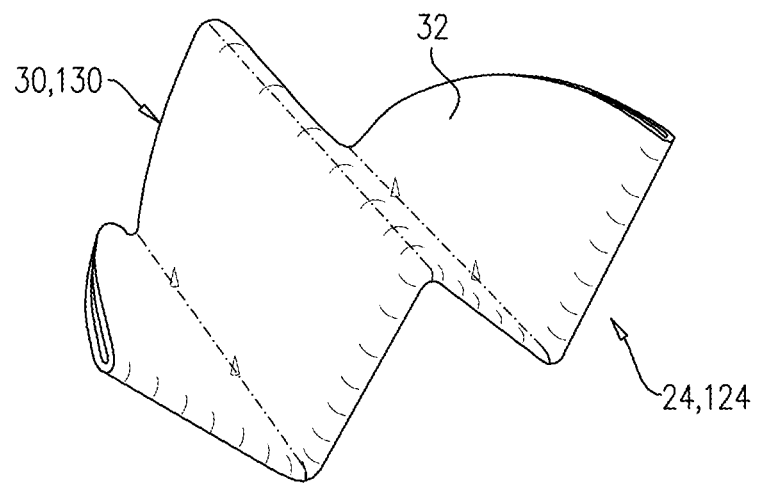
Figure 2F:
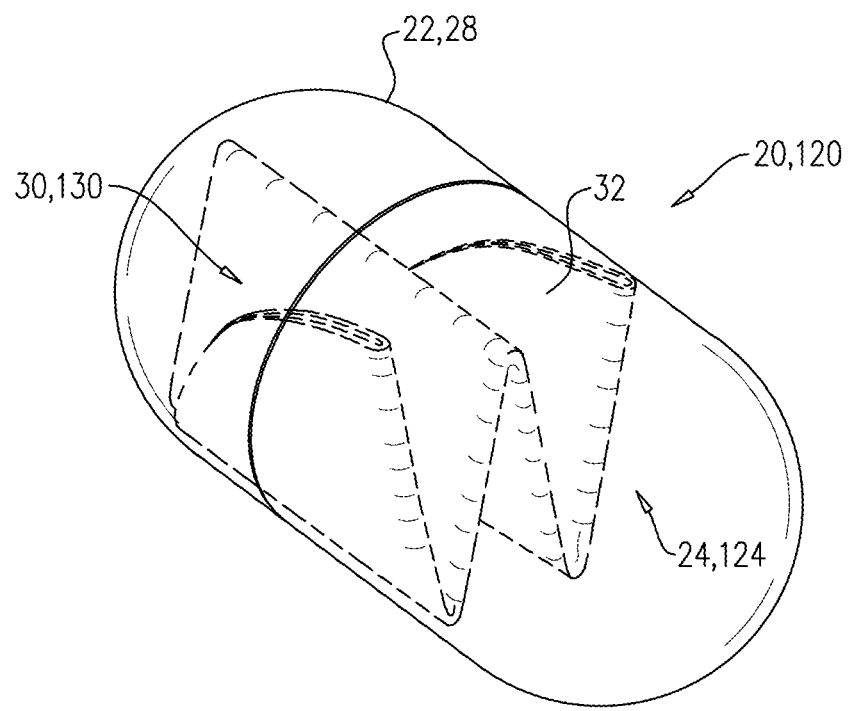

Reference is made to FIGS. 2A-F, which are schematic illustrations of a medication-delivery device 124 of an ingestible pill 120, in accordance with an application of the present invention. FIG. 2A shows medication-delivery device 124 when unconstrained in expanded shape 44, FIGS. 2B-E show medication-delivery device 124 in various stages of folding, and FIG. 2F shows medication-delivery device 124 folded within enteric coating 22. Medication-delivery device 124 is one configuration of medication-delivery device 24, described hereinabove with reference to FIGS. 1A-B, and may implement any of the features described with reference to FIGS. 1A-B. Medication-delivery device 124 comprises a patch 130, which is one configuration of patch 30, described hereinabove with reference to FIGS. 1A-B, and may implement any of the features described with reference to FIGS. 1A-B. In general, the folding pattern and disposition of patch 130 within enteric coating 22 determines which surface of the patch comes in contact with intestinal wall 48 upon dissolving of enteric coating 22.

Figure 3A:
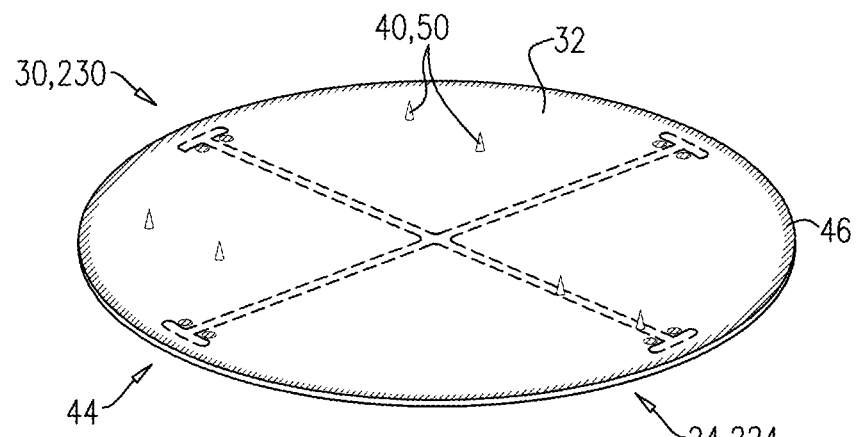
FIGS. 3A-B are schematic illustrations of a medication-delivery device of another ingestible pill, in accordance with an application of the present invention.
Figure 3B:
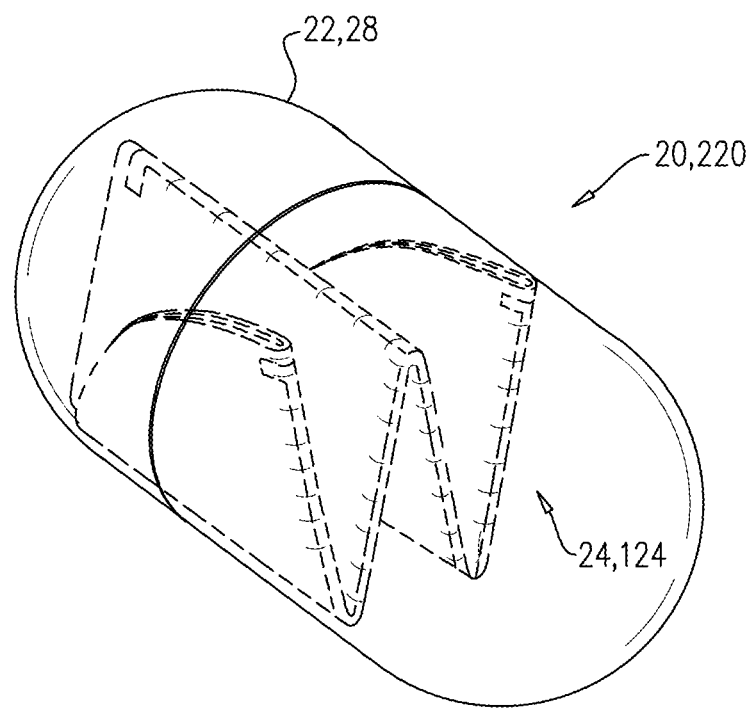

Reference is made to FIGS. 3A-B, which are schematic illustrations of a medication-delivery device 224 of an ingestible pill 220, in accordance with an application of the present invention. FIG. 3A shows medication-delivery device 224 when unconstrained in expanded shape 44, and FIG. 3B shows medication-delivery device 224 folded within enteric coating 22. Medication-delivery device 224 is one configuration of medication-delivery device 24, described hereinabove with reference to FIGS. 1A-B, and may implement any of the features described with reference to FIGS. 1A-B. Other than as described below, medication-delivery device 224 is similar to medication-delivery device 124, and may implement any of the features thereof. Medication-delivery device 224 comprises a patch 230, which is one configuration of patch 30, described hereinabove with reference to FIGS. 1A-B, and may implement any of the features described with reference to FIGS. 1A-B.

Figure 4A:
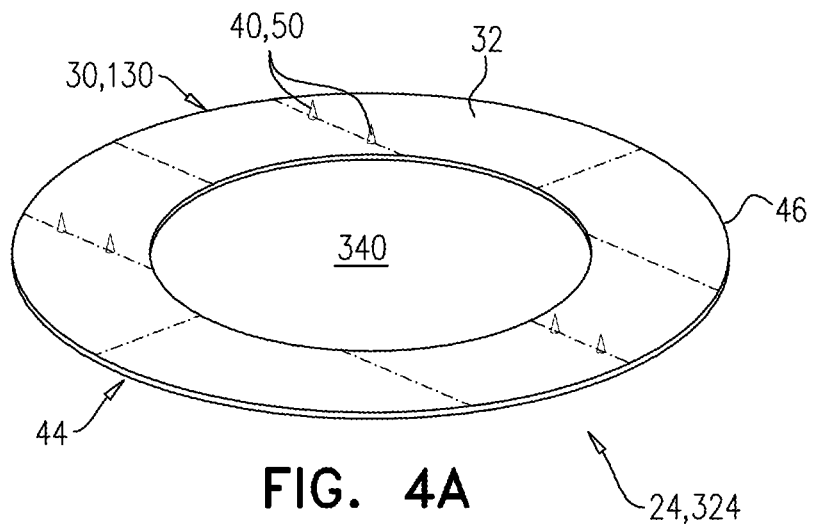
FIGS. 4A-F are schematic illustrations of a medication-delivery device of yet another ingestible pill, in accordance with an application of the present invention.
Figure 4B:
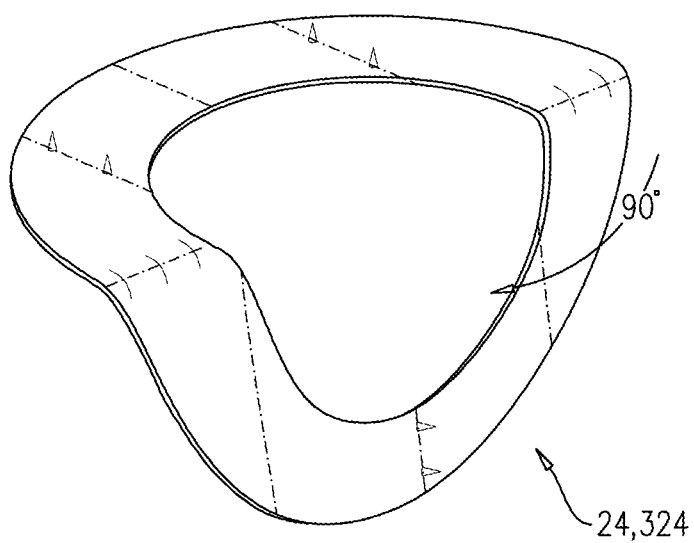
Figure 4C:
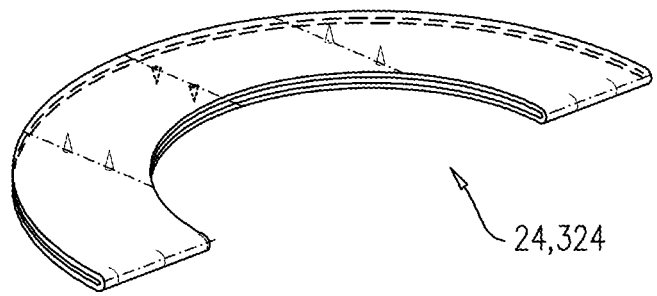
Figure 4D:
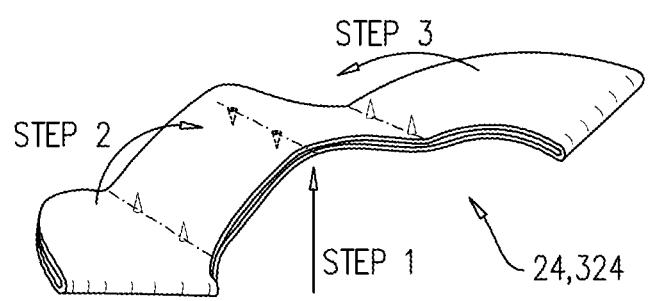
Figure 4E:
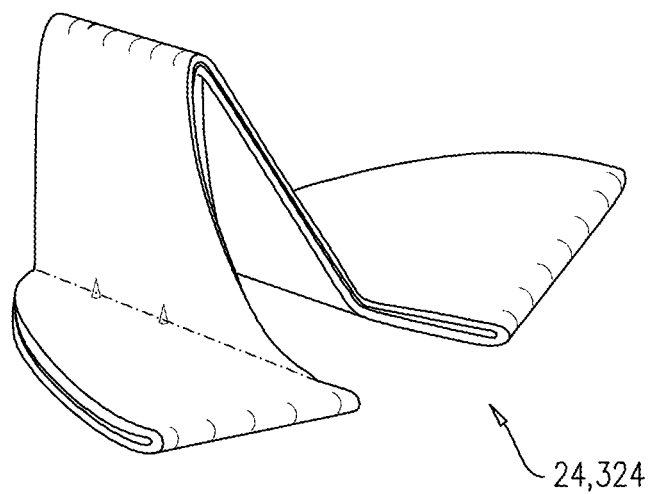
Figure 4F:
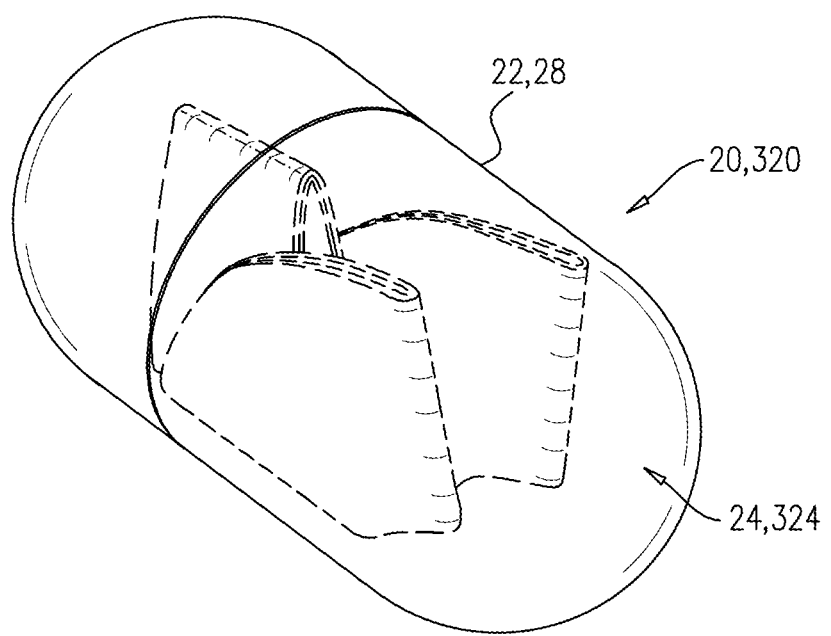

Reference is made to FIGS. 4A-F, which are schematic illustrations of a medication-delivery device 324 of an ingestible pill 320, in accordance with an application of the present invention. FIG. 4A shows medication-delivery device 324 when unconstrained in expanded shape 44, FIGS. 4B-E show medication-delivery device 124 in various stages of folding, and FIG. 4F shows medication-delivery device 324 folded within enteric coating 22. Medication-delivery device 324 is one configuration of medication-delivery device 24, described hereinabove with reference to FIGS. 1A-B, and may implement any of the features described with reference to FIGS. 1A-B. Other than as described below, medication-delivery device 324 is similar to medication-delivery device 124, and may implement any of the features thereof. Medication-delivery device 324 comprises a patch 330, which is one configuration of patch 30, described hereinabove with reference to FIGS. 1A-B, and may implement any of the features described with reference to FIGS. 1A-B.

Figure 5A:
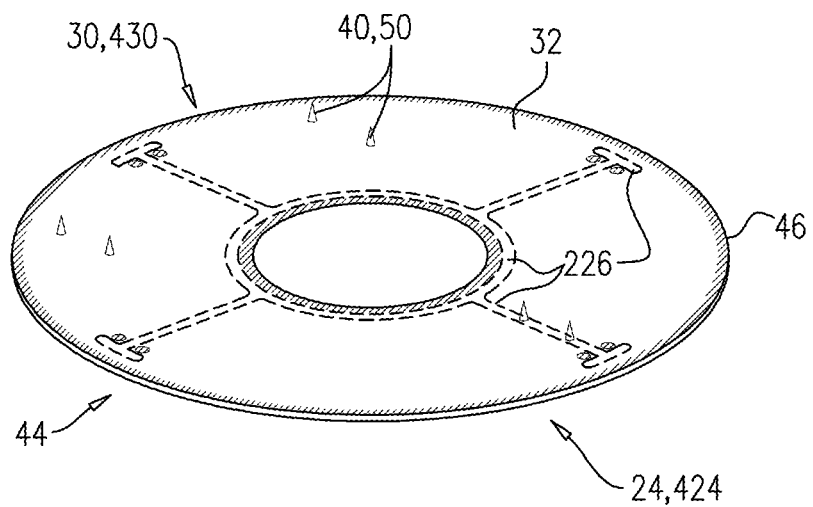
FIGS. 5A-B are schematic illustrations of a medication-delivery device of still another ingestible pill, in accordance with an application of the present invention.
Figure 5B:
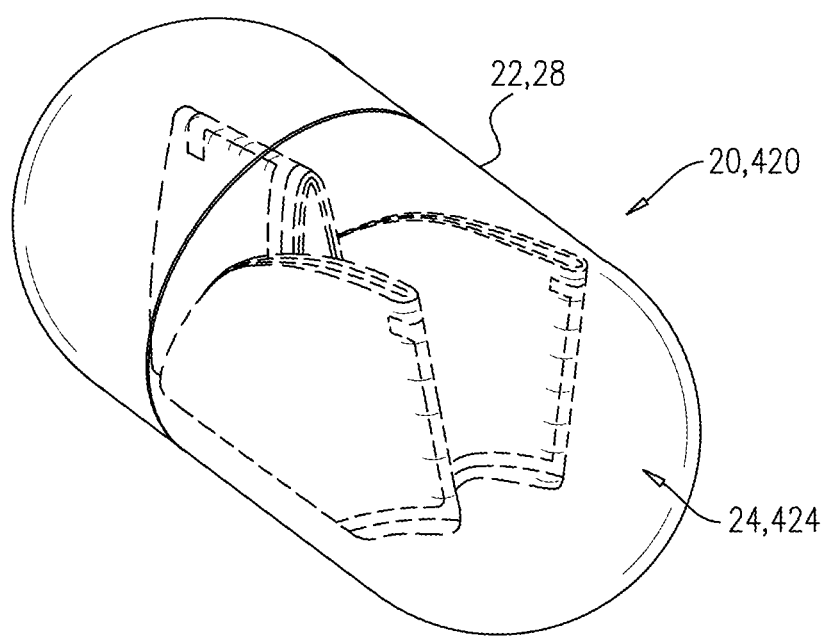

Reference is made to FIGS. 5A-B, which are schematic illustrations of a medication-delivery device 424 of an ingestible pill 420, in accordance with an application of the present invention. FIG. 5A shows medication-delivery device 424 when unconstrained in expanded shape 44, and FIG. 5B shows medication-delivery device 424 folded within enteric coating 22. Medication-delivery device 424 is one configuration of medication-delivery device 24, described hereinabove with reference to FIGS. 1A-B, and may implement any of the features described with reference to FIGS. 1A-B. Other than as described below, medication-delivery device 424 is similar to medication-delivery device 324, and may implement any of the features thereof. Medication-delivery device 424 comprises a patch 130, which is one configuration of patch 430, described hereinabove with reference to FIGS. 1A-B, and may implement any of the features described with reference to FIGS. 1A-B.

Figure 6A:
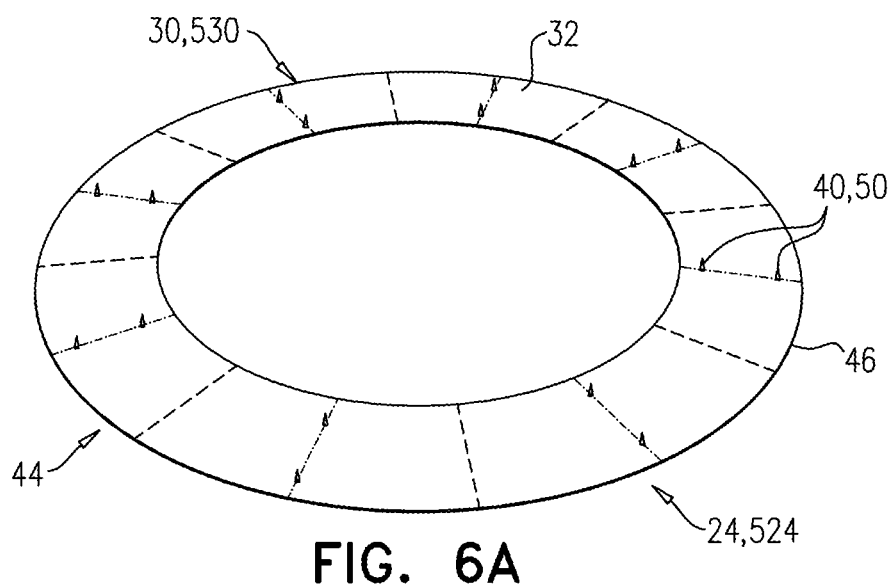
FIGS. 6A-F are schematic illustrations of a medication-delivery device of another ingestible pill, in accordance with an application of the present invention.
Figure 6B:
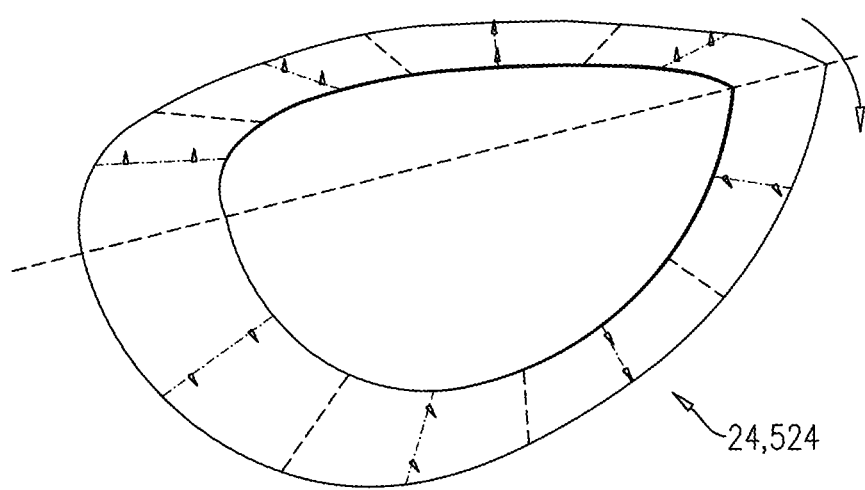
Figure 6C:
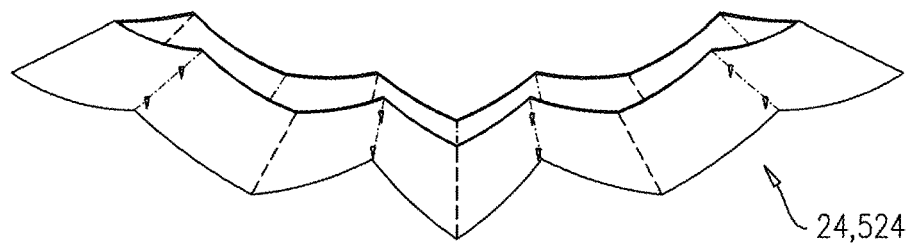
Figure 6D:
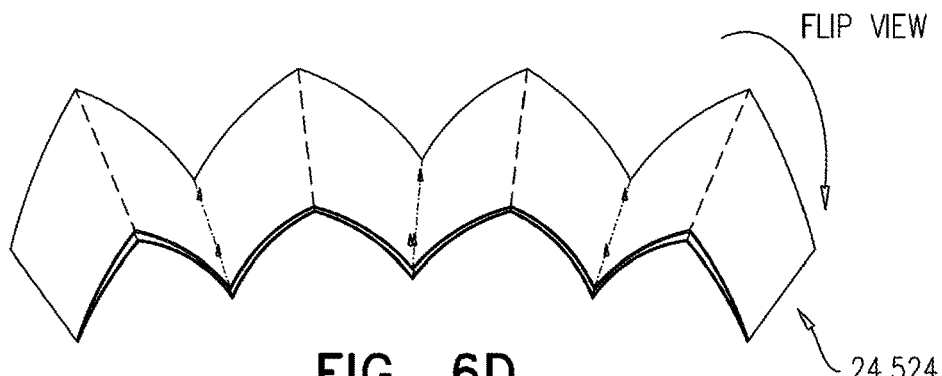
Figure 6E:
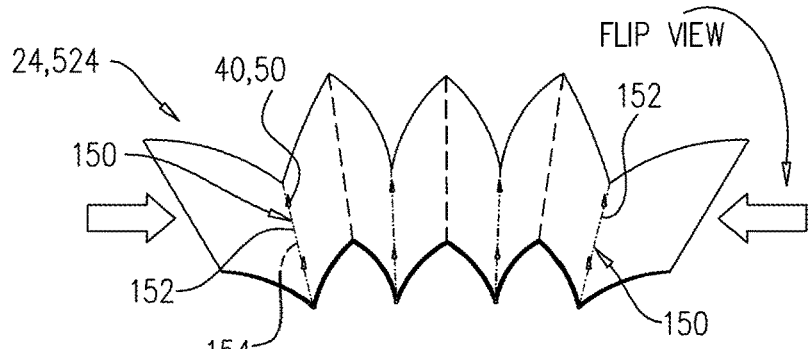
Figure 6F:
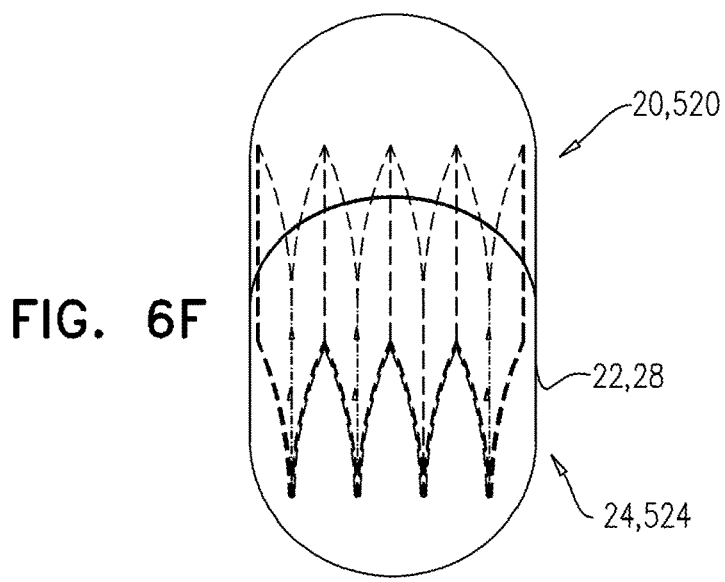

Reference is made to FIGS. 6A-F, which are schematic illustrations of a medication-delivery device 524 of an ingestible pill 520, in accordance with an application of the present invention. FIG. 6A shows medication-delivery device 524 when unconstrained in expanded shape 44, FIGS. 6B-E show medication-delivery device 124 in various stages of folding, and FIG. 6F shows medication-delivery device 524 folded within enteric coating 22. Medication-delivery device 524 is one configuration of medication-delivery device 24, described hereinabove with reference to FIGS. 1A-B, and may implement any of the features described with reference to FIGS. 1A-B. Other than as described below, medication-delivery device 524 is similar to medication-delivery device 324, and may implement any of the features thereof. Medication-delivery device 524 comprises a patch 530, which is one configuration of patch 30, described hereinabove with reference to FIGS. 1A-B, and may implement any of the features described with reference to FIGS. 1A-B.

Reference is made to FIGS. 2A-F, 3A-B, 4A-F, 5A-B, and 6A-F. As shown in FIGS. 2F, 3B, 4F, 5B, and 6F, patch 30 is disposed within enteric coating 22, folded so as to define one or more creases 150 (e.g., a plurality of creases 150), which define respective inner crease sides 152 and outer crease sides 154. The formation of these creases is illustrated in FIGS. 2A-E, 3A, 4A-E, 5A, and 6A-E, respectively. As used in the present application, including in the claims, a "crease" is a sharp, well-defined fold. For some applications, at least 50% (such as at least 75%, e.g., at least 90%, e.g., 100%) of needles 40 are coupled (e.g., adhered) to patch 30 along inner crease sides 152. Coupling needles 40 to patch along inner crease sides 152 helps protect the needles from being broken during folding of the patch and stabilizes the needles on either side of the crease, and helps avoiding deflecting the needles from the plane of the surface when the patch is folded.

For some applications, patch 30 is disposed within enteric coating 22, folded first in half (as can perhaps best be seen in FIGS. 2B-C, 4B-C, and 6B), and then accordion-folded, as can be seen in FIGS. 2D-F, 3B, 4D-F, 5B, and 6C-F.

Typically, patch 30 is disposed within enteric coating 22, folded such that when patch 30 assumes expanded shape 44 upon dissolving of enteric coating 22 in small intestine 26, upper surface 32 of patch 30 contacts intestinal wall 48, thereby bringing needles 40 into contact with intestinal wall 48. In other words, the folding of patch 30 within enteric coating 22 typically determines which surface of patch 30 comes in contact with intestinal wall 48.

Typically, needles 40 are not coupled to respective inner crease sides 152 of a portion of creases 150. Also typically, needles 40 are not coupled to respective inner crease sides 152 of two or more of creases 150.

For some applications, at least 50%, such as at least 80%, e.g., 100%, of needles 40 are coupled to upper surface 32 of patch 30 when patch 30 is disposed within enteric coating 22. Alternatively or additionally, for some applications, at least 50% of needles 40 are coupled to upper surface 32 of patch 30 along inner crease sides 152 when patch 30 is disposed within enteric coating 22.

Typically, between 0% (i.e., none) and 10% of needles 40 are coupled to patch 30 along outer crease sides 154 when patch 30 is disposed within enteric coating 22.

Reference is made to FIGS. 2A, 3A, 4A, 5A, and 6A, which show patch 30 generally flat in expanded shape 44 when medication-delivery device 24 is unconstrained. For some applications, patch 30 can inscribe a circle having a diameter of at least 2 cm, less than 10 cm (e.g., less than 7 cm, such as less than 5 cm), and/or between 2 and 10 cm, e.g., between 2 and 7 cm, such as between 2 and 5 cm), when patch 30 assumes expanded shape 44 and is unconstrained. This diameter may allow patch 30 to circumscribe at least 180 degrees of the intestinal lumen, but typically not more than 360 degrees. (As is known in the art, an inscribed circle is the largest possible circle that can be drawn on the inside of a plane figure. It is noted that the circle is a geometric shape used to describe patch 30, and is not an element of the invention.) Alternatively or additionally, for applications in which patch 30 is circular, the diameter of patch 30 is typically greater than $\pi$ (pi) times the radius of small intestine 26, and/or greater than 60 mm or between 65 mm and 150 mm, such that patch 30 extends around at least 180 degrees of a circumference of small intestine 26 when expanded in small intestine 26.

Reference is made to FIGS. 4A-F, 5A-B, 6A-F, and 13A-D. In the configurations shown in these figures, patch 30 is annular, i.e., is shaped as a ring defining an opening 340 therethrough when unconstrained in expanded shape 44, as shown in FIGS. 4A, 5A, 6A, and 13A-D. Opening 340 may allow for compression of medication-delivery device 24 when in compressed shape 42 when disposed within enteric coating 22, while still providing good contact with intestinal wall 48 when in expanded shape 44.

Reference is made to FIGS. 3A-B and 5A-B. In the configurations shown in these figures, patch 30 comprises a non-metal material, and medication-delivery device 224, 424 further comprises elastic struts 226, which are fixed to patch 30. Elastic struts 226 are configured, upon enteric coating 22 dissolving, to transition medication-delivery device 224, 424 from the compressed shape to expanded shape 44.

For some applications, elastic struts 226 comprise metal, such as a shape memory alloy, such as Nitinol. The low stress of the shape memory alloy when the medication-delivery device has compressed shape 42 when disposed within coating 22 reduces the likelihood of the medication-delivery device forgetting its memorized shape. Alternatively, for some applications, struts 226 comprise stainless steel.

Optionally, patch 30 comprises a plurality of layers, which are fixed together (for example, fused (e.g., welded) or glued together) at one or more fixation locations 768, such as shown, for example, in FIGS. 9A-B and 10A-B. All of the layers described herein may comprise one or more pieces of material, and multiple layers may optionally be formed from a single folded piece of material. The layers described herein comprise a broad, thin, pliable material, e.g., a membrane.

Reference is made to FIGS. 7A-13D, which are schematic illustrations of several configurations of a medication-delivery device 624, in accordance with respective applications of the present invention. Medication-delivery device 624 may implement any of the features of medication-delivery device 24, described hereinabove with reference to FIGS. 1A-6F. Medication-delivery device is a component of ingestible pill 20 (which comprises enteric coating 22), described hereinabove with reference to FIGS. 1A-6F.

Figure 7A:
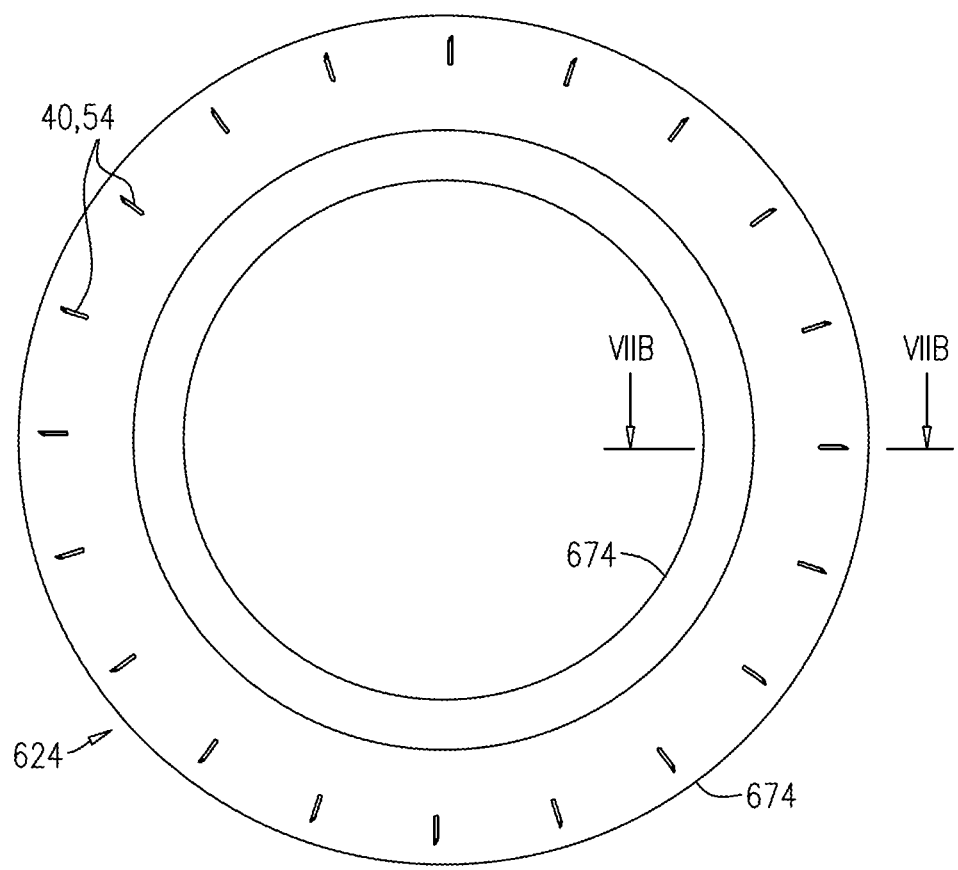
FIGS. 7A-C are schematic illustrations of a medication-delivery device of an ingestible pill, in accordance with an application of the present invention.
Figure 7B:
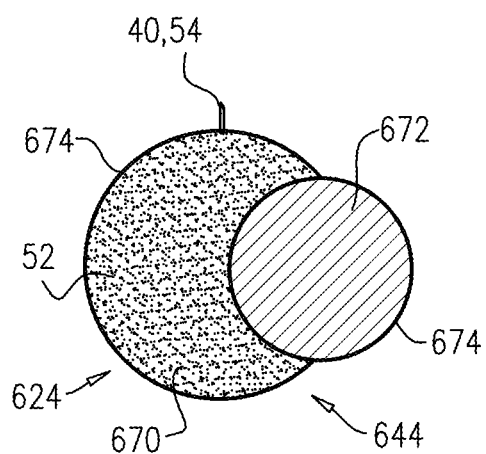
Figure 7C:
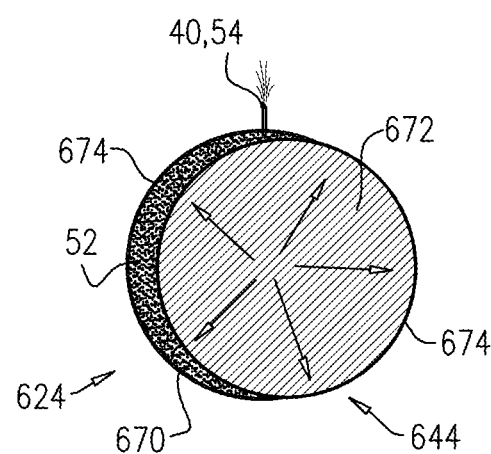
Figure 8A:
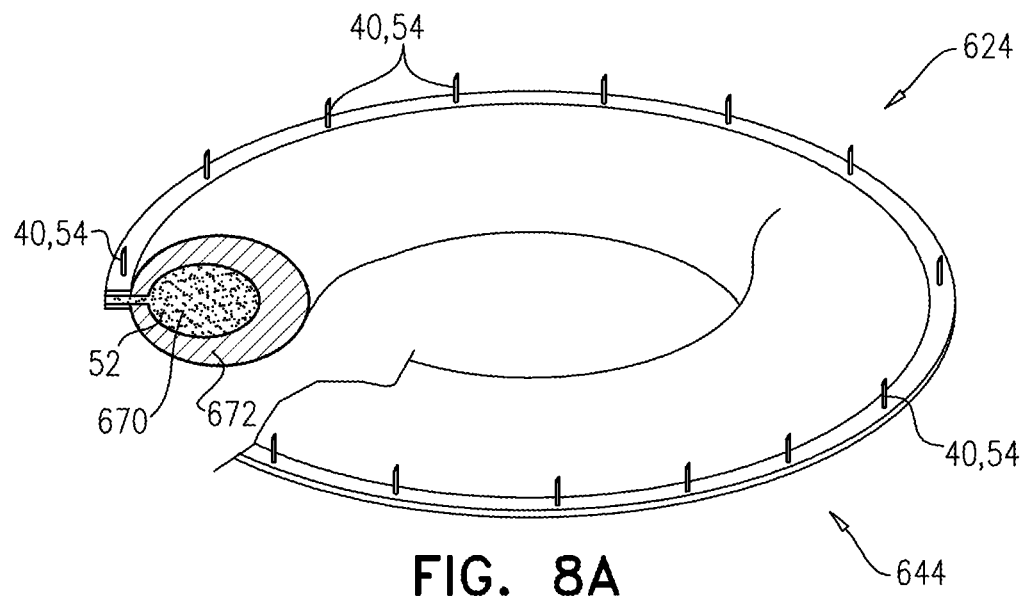
FIGS. 8A-B are schematic illustration of a medication-delivery device of an ingestible pill, in accordance with an application of the present invention.
Figure 8B:
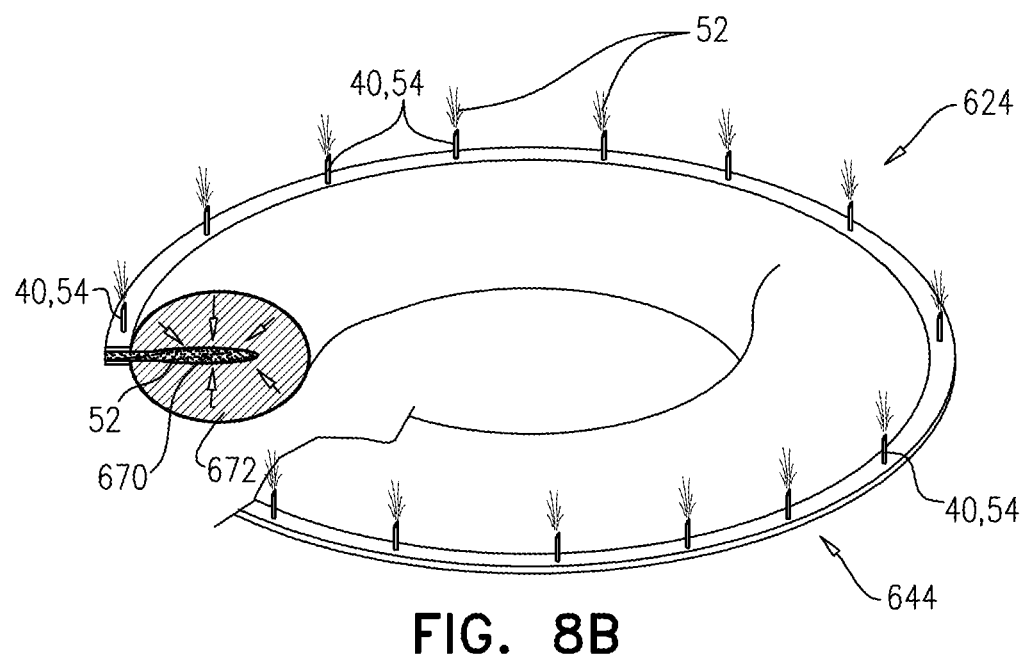

FIGS. 7A-C show medication-delivery device 624 in an expanded shape 644 after enteric coating 22 dissolves. FIG. 7B shows medication-delivery device 624 before expansion of one or more expansible chambers 672, as described below. FIGS. 7A and 7C show medication-delivery device 624 upon expansion of the one or more expansible chambers 672, as described below.

In the configurations described with reference to FIGS. 7A-13D, medication-delivery device 624 is pliable, i.e., easily bent and flexible, as opposed to stiff or rigid. Medication-delivery device 624 is disposed within enteric coating 22, having a compressed shape enabled by the pliability (similar to the configuration shown in FIG. 1A). The pliability also typically helps medication-delivery device 624 conform with intestinal wall 48 when in expanded shape 644.

Medication-delivery device 624 is shaped so as to define one or more medication chambers 670 and one or more expansible chambers 672. Medication-delivery device 624 comprises:
one or more outer surfaces 674, all of which are pliable;
hollow medication-delivery needles 54, which are coupled to at least one of the one or more outer surfaces 674; and
medication 52, which is contained within the one or more medication chambers 670.

Medication-delivery device 624 is configured to assume, after enteric coating 22 dissolves, expanded shape 644 in which hollow medication-delivery needles 54 (a) are in fluid communication with the one or more medication chambers 670 and (b) extend away from medication-delivery device 624. Medication-delivery device 624 is configured such that expansion of the one or more expansible chambers 672 forces medication 52 from the one or more medication chambers 670 and out of medication-delivery device 624 through hollow medication-delivery needles 54. For example, medication 52 may comprise a liquid, or a solid that dissolves upon exposure to bodily fluids.

For some applications, the one or more expansible chambers 672 comprise one or more inflatable chambers. For some applications, the one or more inflatable chambers contain a substance that produces gas upon contact with liquid, such as described hereinbelow with reference to FIGS. 9A-B.

For some applications, at least one of the one or more outer surfaces 674 comprises biocellulose (also known in the art as microbial cellulose and bacterial cellulose), which is liquid-permeable and substantially not gas-permeable.

Reference is made to FIGS. 7A-8B. For some applications, medication-delivery device 624 is shaped as a circular or elliptical torus. The toroidal shape provides the above-mentioned structure.

Reference is made to FIGS. 9A-13D. For some applications, medication-delivery device 624 is shaped as a patch 30.

Figure 9A:
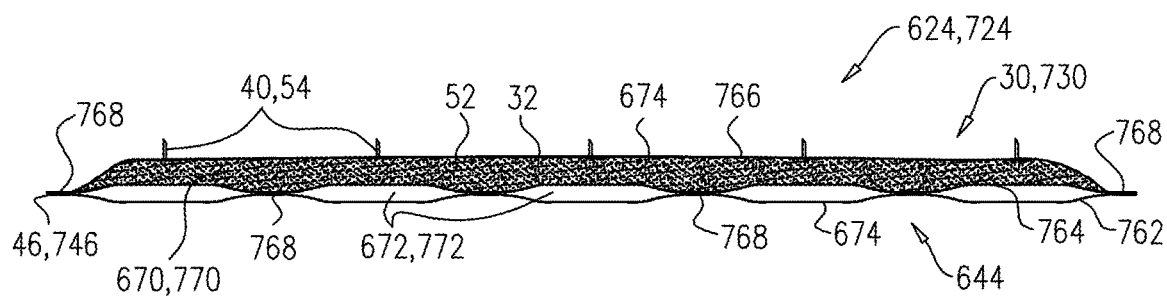
FIGS. 9A-B are schematic illustrations of a medication-delivery device of an ingestible pill, in accordance with an application of the present invention.
Figure 9B:
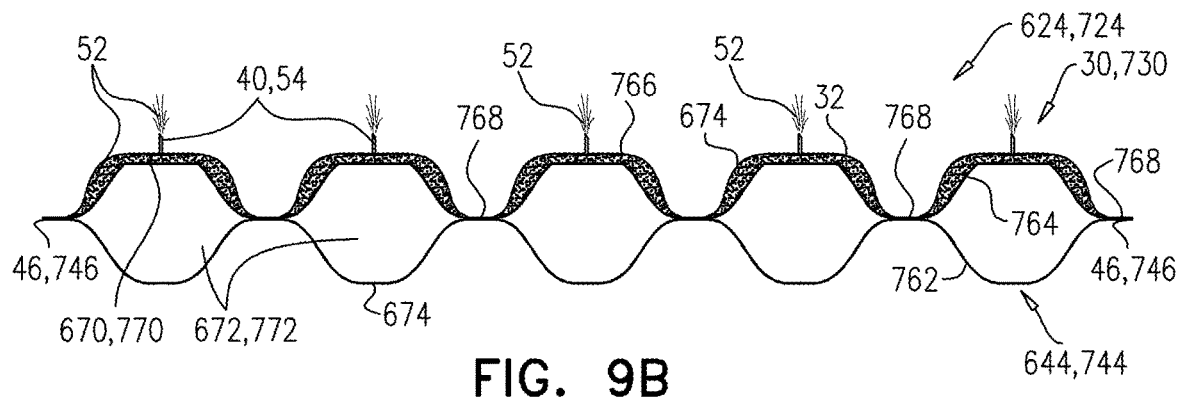

Reference is made to FIGS. 9A-B, which are schematic illustrations of a medication-delivery device 724, in accordance with an application of the present invention. FIG. 9A shows medication-delivery device 724 after enteric coating 22 has dissolved. FIG. 9B shows medication-delivery device 724 after expansion of expansible chambers 672, 772, as described hereinbelow. Medication-delivery device 724 is one implementation of medication-delivery device 624, described hereinabove, and may implement any of the features thereof. In addition, medication-delivery device 724 may implement any of the features of the medication-delivery devices described herein with reference to FIGS. 1A-B, 2A-F, 3A-B, 4A-F, 5A-B, 6A-F, 11A-B, 12A-C, and/or 13A-D.

Medication-delivery device 724 is a component of an ingestible pill comprising enteric coating 22. Medication-delivery device 724 comprises a patch 730, which has a compressed shape when disposed within enteric coating 22, and which is shaped so as to define an outer perimeter 46, 746, and which comprises at least a first layer 762, a second layer 764, and a third layer 766, which are arranged so as to define:
one or more medication chambers 670, 770 between second layer 764 and third layer 766, and
one or more expansible chambers 672, 772 between first layer 762 and second layer 764.

First layer 762 and second layer 764 are fixed together at fixation locations 768, for example, fused (e.g., welded) or glued together. Some of fixation locations 768 are located at or near outer perimeter 760 and some of fixation locations 768 are located at least 2 mm from outer perimeter 760. Fixation locations 768 generally at least partially divide an interior of the one or more expansible chambers 672, 772 into sub-chambers, which help maintain patch 730 fairly flat even upon inflation.

Medication-delivery device 724 further comprises medication 52, which is contained within the one or more medication chambers 670, 770.

Patch 730 is configured to assume, after enteric coating 22 dissolves, an expanded shape 644, 744, such as shown in FIG. 9B.

Third layer 766 is permeable to medication 52, such that expansion of the one or more expansible chambers 672, 772 forces medication 52 from the one or more medication chambers 670, 770, through third layer 766, and out of medication-delivery device 724. Third layer 766 thus serves as upper surface 32 of patch 730 that contact intestinal wall 48, as described hereinabove.

For some applications, the one or more expansible chambers 672, 772 comprise one or more inflatable chambers. Typically, the one or more inflatable chambers contain a substance that produces gas upon contact with liquid. For example, the substance may comprise sodium bicarbonate and/or citric acid (e.g., 60-70% sodium bicarbonate and 30-40% citric acid). For some applications, first layer 762 is liquid-permeable and substantially not gas-permeable, in order to allow bodily fluids to pass into the one or more expansible chambers 672, 772 and contact the substance that produces the gas. For example, first layer 762 may comprise biocellulose. Optionally, the entire patch 730, except the upper surface that faces the intestinal wall, comprises biocellulose.

For other applications, the one or more expansible chambers 672, 772 contain a substance that expands upon contact with liquid. For example, the substance may comprise a polymer, such as a hydrogel.

For some applications, patch 730 can inscribe a circle having a diameter of at least 2 cm, less than 10 cm (e.g., less than 7 cm, such as less than 5 cm), and/or between 2 and 10 cm, e.g., between 2 and 7 cm, such as between 2 and 5 cm), when patch 30 assumes expanded shape 644, 744. Typically, patch 730 is configured such that expanded shape 644, 744 is generally flat when medication-delivery device 724 is unconstrained and becomes curved by intestinal wall 48.

For some applications, medication-delivery device 724 comprises a plurality of hollow medication-delivery needles 40, 54, which are coupled to third layer 766 in fluid communication with the one or more medication chambers 670 when medication-delivery device 724 is in expanded shape 644, 744, and extend away from patch 730 when patch 730 assumes expanded shape 644, 744. Typically, the ingestible pill is configured such that when patch 730 assumes expanded shape 644, 744 upon dissolving of enteric coating 22 in small intestine 26, third layer 766 of patch 30 contacts intestinal wall 48, thereby bringing hollow medication-delivery needles 54 into contact with intestinal wall 48.

For other applications, third layer 766 is shaped so as to define one or more pores that provide the permeability.

Figure 10A:
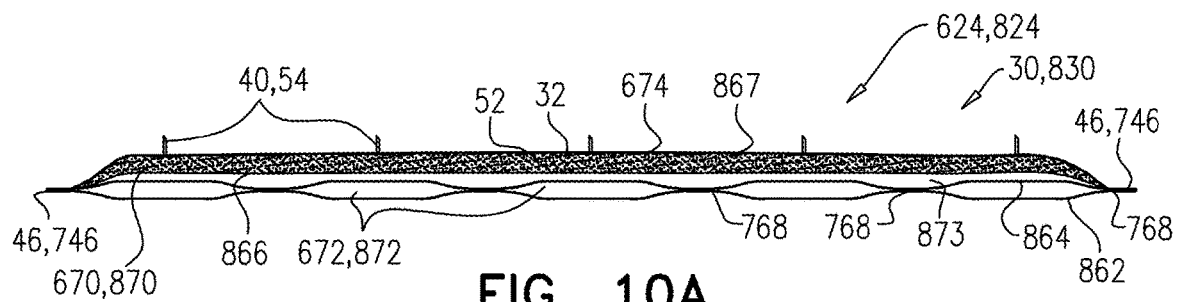
FIGS. 10A-B are schematic illustrations of a medication-delivery device of an ingestible pill, in accordance with an application of the present invention.
Figure 10B:
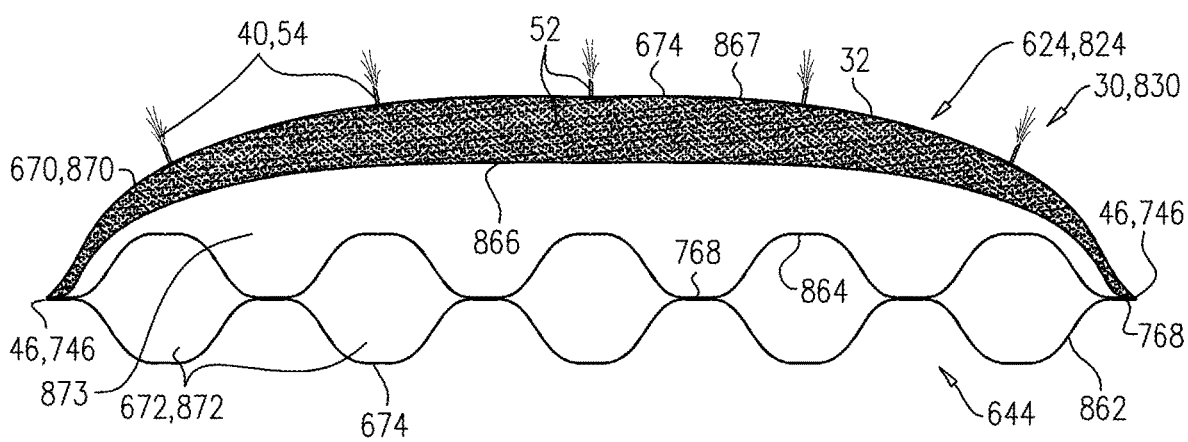

Reference is made to FIGS. 10A-B, which are schematic illustrations of a medication-delivery device 824, in accordance with an application of the present invention. FIG. 10A shows medication-delivery device 824 after enteric coating 22 has dissolved. FIG. 10B shows medication-delivery device 824 after expansion of first expansible chambers 873 and second expansible chambers 672, 872, as described hereinbelow. Medication-delivery device 824 is one implementation of medication-delivery device 624, described hereinabove, and may implement any of the features thereof. In addition, medication-delivery device 824 may implement any of the features of the medication-delivery devices described herein with reference to FIGS. 1A-B, 2A-F, 3A-B, 4A-F, 5A-B, 6A-F, 9A-B, 11A-B, 12A-C, and/or 13A-D.

Other than as described below, medication-delivery device 824 is identical to medication-delivery device 724, described hereinabove with reference to FIGS. 9A-B.

A patch 830 of medication-delivery device 824 comprises at least a first layer 862, a second layer 864, a third layer 866, and a fourth layer 867, which are arranged so as to define:
one or more medication chambers 670, 870 between third layer 866 and fourth layer 867,
one or more first expansible chambers 873 between second layer 864 and third layer 866, and
one or more second expansible chambers 672, 872 between first layer 862 and second layer 864.

First layer 862 and second layer 864 are fixed together at fixation locations 768. Some of the fixation locations 868 are located at or near outer perimeter 46, 746 and some of fixation locations 768 are located at least 2 mm from outer perimeter 46, 746.

Fourth layer 867 is permeable to medication 52, such that expansion of the one or more second expansible chambers 672, 872 forces medication 52 from the one or more medication chambers 670, 870, through fourth layer 867, and out of medication-delivery device 824. Fourth layer 867 thus serves as upper surface 32 of patch 830 that contact intestinal wall 48, as described hereinabove.

For some applications, medication-delivery device 824 is configured such that upon contact with liquid, the one or more second expansible chambers 672, 872 begin to expand before the one or more first expansible chambers 873 begin to expand. For example, the liquid may have separate access to the one or more second expansible chambers 672, 872 and the one or more first expansible chambers 873, and a physical property of the one of or more of the layers is configured to control timing. For some applications, the one or more first expansible chambers 873 comprise one or more first inflatable chambers, and second layer 864 is gas-permeable, such that upon inflation of the one or more second inflatable chambers, gas passes from the one or more second inflatable chambers through the gas-permeable second layer 864 to the one or more first inflatable chambers, such that the one or more second inflatable chambers begin to inflate before the one or more first inflatable chambers begin to inflate, which in turn force the medication 52 through fourth layer 867. For some applications, second layer 864 is shaped so as define a plurality of pores (i.e., small holes) that provides the gas-permeability. Alternatively or additionally, for some applications, second layer 864 is configured to tear upon inflation of the one or more second inflatable chambers, thereby providing the gas-permeability.

For some applications, first layer 862 is liquid-permeable and substantially not gas-permeable, such as described above with reference to FIGS. 9A-B. For example, first layer 862 may comprise biocellulose.

For some applications, second layer 864 is liquid-permeable and substantially not gas-permeable. For some applications, first layer 862 comprises biocellulose.

Figure 11A:
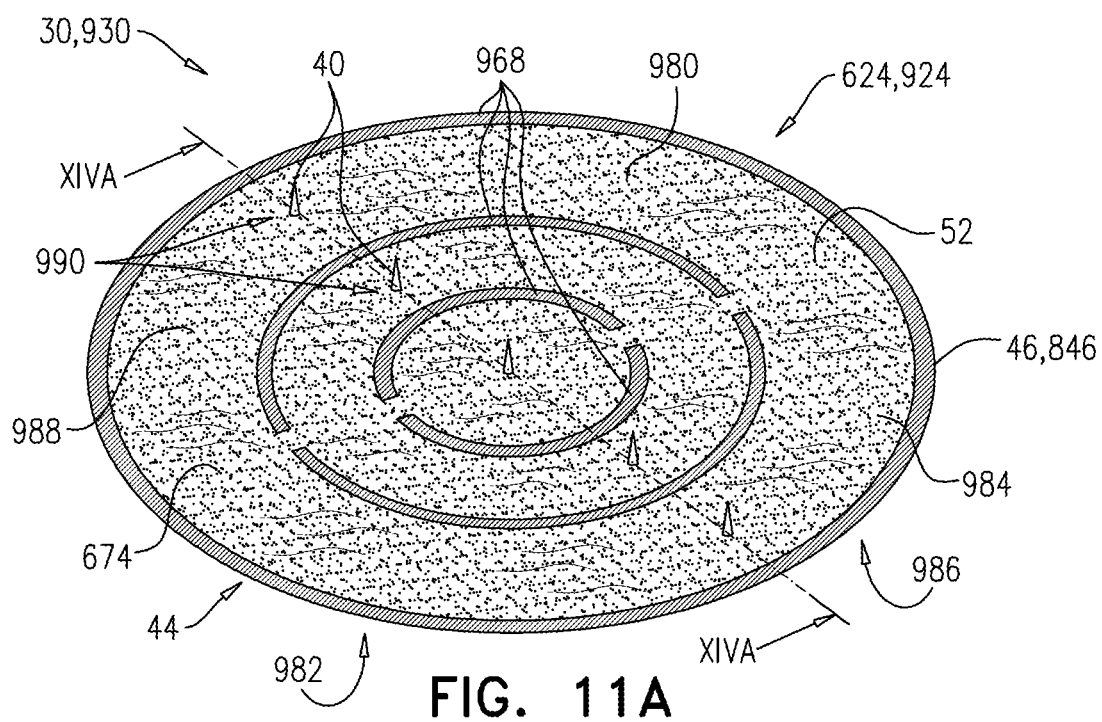
FIGS. 11A-B are schematic illustrations of a medication-delivery device of an ingestible pill, in accordance with an application of the present invention.
Figure 11B:
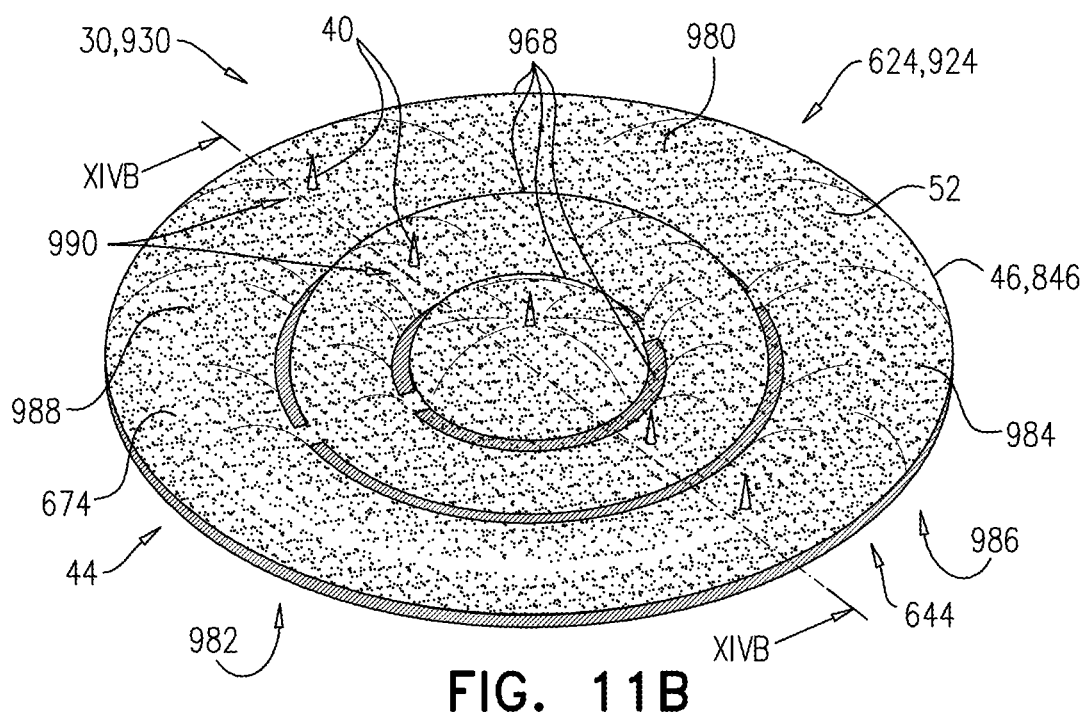
Figure 12A:
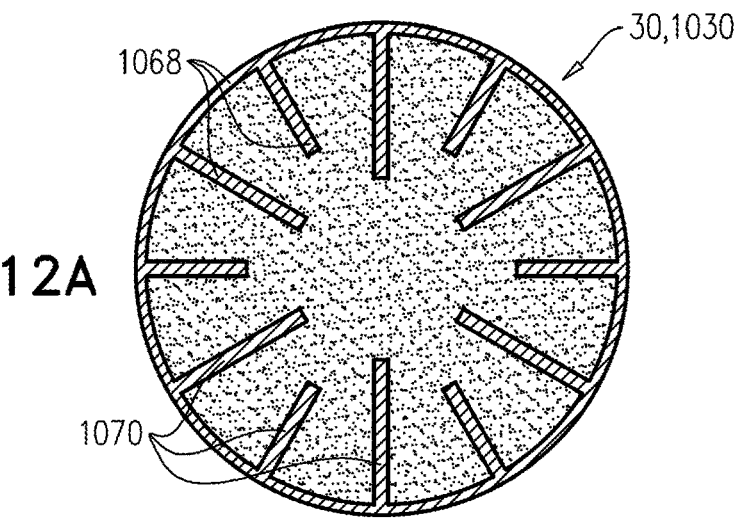
FIGS. 12A-C which are schematic illustrations of configurations of a patch, in accordance with respective applications of the present invention.
Figure 12B:
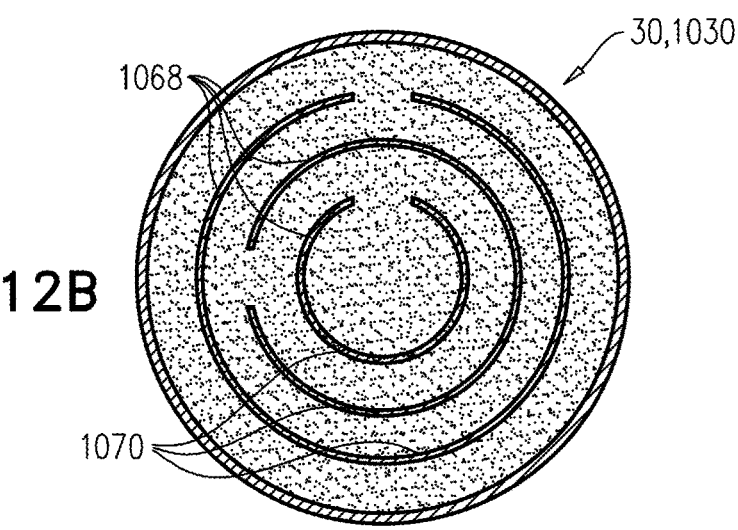
Figure 12C:
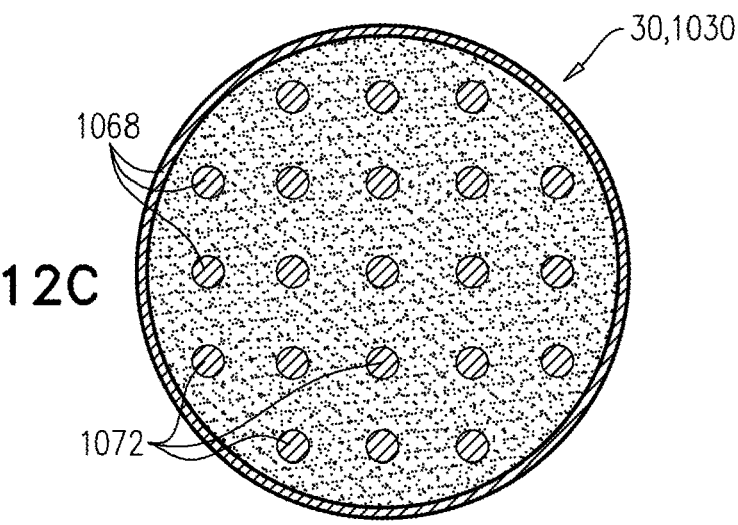
Figure 13A:
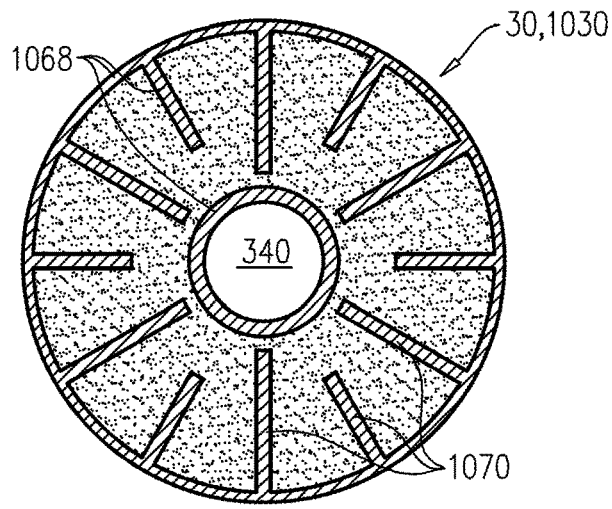
FIGS. 13A-D are schematic illustrations of configurations of another patch, in accordance with respective applications of the present invention.
Figure 13B:
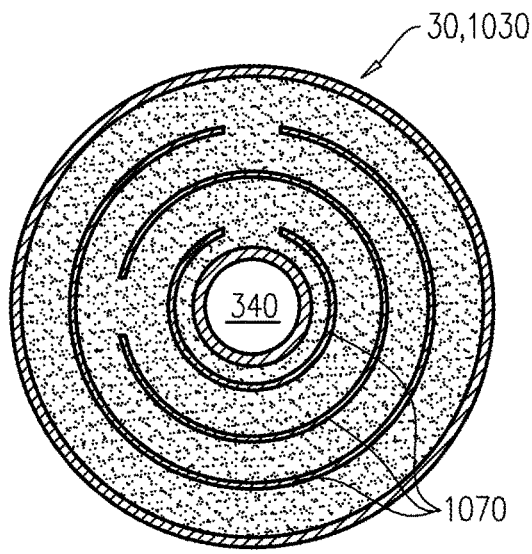
Figure 13C:
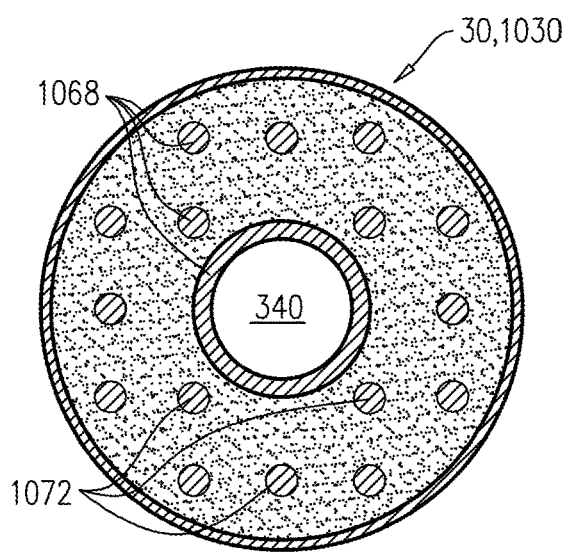
Figure 13D:
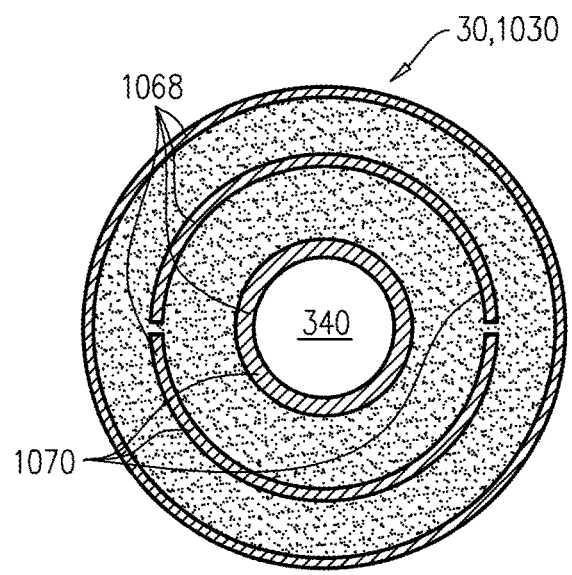

Reference is again made to FIGS. 9A-B and 10A-B, and is additionally made to FIGS. 11A-B, which are schematic illustrations of a medication-delivery device 924, in accordance with an application of the present invention. Medication-delivery device 924 is a component of an ingestible pill comprising enteric coating 22. Medication-delivery device 924 is one implementation of medication-delivery device 624, described hereinabove, and may implement any of the features thereof. In addition, medication-delivery device 924 may implement any of the features of the medication-delivery devices described herein with reference to FIGS. 1A-B, 2A-F, 3A-B, 4A-F, 5A-B, 6A-F, 10A-B, 12A-C, and/or 13A-D.

FIG. 11A shows medication-delivery device 924 after enteric coating 22 has dissolved. FIG. 11B shows medication-delivery device 924 after expansion of expansible chambers 988 thereof. For example, medication-delivery device 924 may be shaped so as to define expansible chambers 772, such as described hereinabove with reference to FIGS. 9A-B, or first expansible chambers 873 and second expansible chambers 872, such as described hereinabove with reference to FIGS. 10A-B. The expansible chambers may implement any of the features of the expansible chambers described herein.

Medication-delivery device 924 comprises (a) a patch 930, which has a compressed shape when disposed within enteric coating 22, and which is shaped so as to define an outer perimeter 46, 846, and (b) needles 40.

Patch 930 has an upper surface 980 and a lower surface 982 that face in generally opposite directions. Patch 930 (iv) comprises at least a first layer 984 and a second layer 986, which are arranged so as to define one or more expansible chambers 988 between first layer 984 and second layer 986. First layer 984 and second layer 986 are fixed together at fixation locations 968. Typically, some of fixation locations 968 are located at or near outer perimeter 46, 846 and some of fixation locations 968 are located at least 2 mm from outer perimeter 46, 846. Needles 40 are coupled to upper surface 980 at respective needle locations 990.

Patch 930 is configured such that, if patch 930 were laid generally flat on a flat horizontal surface, at least 80%, e.g., at least 90%, such as all, of needle locations 990 would be horizontally offset from fixation locations 968. As used in the present application, including in the claims, "horizontally" means in a direction along the plane defined by the flat horizontal surface. It is noted that flat horizontal surface is not an element of the invention, but instead is a geometric shape used to define certain structural features of the invention. The invention does not require actually placing the patch laid flat on the flat horizontal surface.

For some applications, patch 930 is configured such that, if patch 930 were laid generally flat on the flat horizontal surface, needle locations 990 would be located on average at least 1 mm (e.g., at least 2 mm, such as at least 3 mm, e.g., at least 5 mm) horizontally from respective nearest fixation locations 968. For some applications, patch 930 is configured such that, if patch 930 were laid generally flat on the flat horizontal surface, each of needle locations 990 would be located at least 1 mm (e.g., at least 2 mm, such as at least 3 mm, e.g., at least 5 mm) horizontally from a nearest one of fixation locations 968.

For some applications, patch 930 is configured such that, if patch 930 were laid generally flat on the flat horizontal surface, each of needle locations 990 would be located approximately horizontally centered between a nearest two of fixation locations 968.

The arrangements of needle locations 990 with respect to fixation locations 968 described above result in needles 40 being generally located at or near local peaks of upper surface 980 between valleys defined by fixation locations 968. These relatively high locations may help maximize the puncturing of needles 40 through villi of intestinal wall 48 with as short as possible needles, and with minimal risk of blocking the needles with the expandable chamber before all of the drug is expelled (i.e., with minimum residual drug).

Needles 40 may have any of the features described herein. For example, the needles may comprise a solid medication, or may be configured to deliver a medication contained in medication-delivery device 924, such as in one or more medication chambers, such as described herein.

For some applications, patch 930 is disposed within enteric coating 22, folded so as to define one or more creases (e.g., a plurality of creases), which define respective inner and outer crease sides, and wherein at least 50% of the needles are coupled to upper surface 980 of patch 930 along the inner crease sides, such as described hereinabove with reference to FIGS. 2A-F, 3A-B, 4A-F, 5A-B, and 6A-F.

For some applications, patch 930 can inscribe a circle having a diameter of at least 2 cm, less than 10 cm (e.g., less than 7 cm, such as less than 5 cm), and/or between 2 and 10 cm, e.g., between 2 and 7 cm, such as between 2 and 5 cm), when patch 930 assumes the expanded shape and is unconstrained.

Reference is now made to FIGS. 12A-C and 13A-D, which are schematic illustrations of configurations of a patch 30, 1030, in accordance with respective applications of the present invention. Any of the patches described herein that have fixation locations may implement any of these configurations. Fixation locations 1068 of patch 30, 1030 are between two or more layers of patch 30, 1030, as described hereinabove.

For some applications, at least some of fixation locations 1068 are arranged in a plurality of segments 1070. For some applications, at least some of segments 1070 are curved when patch 30 assumes expanded shape 44. For some of these applications, at least some of the curved segments 1070 are arranged equidistantly around a center point of patch 30 when patch 30 assumes expanded shape 44. For some applications, at least some of segments 1070 are straight when patch 30 assumes expanded shape 44. For some of these applications, at least some of straight segments are arranged radially when patch 30 assumes expanded shape 44, and may not reach a center point of the patch.

Alternatively or additionally, at least some of fixation locations 768 are arranged in a plurality of points 1072. As used in the present application, including the claims, "points" are small point-like areas rather than literal zero-dimensional points.

In an embodiment, techniques and apparatus described in one or more of the following applications are combined with techniques and apparatus described herein:

U.S. Pat. No. 8,287,902 to Gross; and/or

U.S. Pat. No. 9,492,396 to Gross.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An ingestible pill comprising:
an enteric coating; and
a medication-delivery device, which comprises (a) a patch having upper and lower surfaces that face in generally opposite directions; and (b) needles, wherein the patch is disposed within the enteric coating, folded so as to define one or more creases, which define respective inner and outer crease sides, wherein at least one of the needles is coupled to the patch along the inner crease sides, and
wherein the patch is configured to assume, after the enteric coating dissolves, an expanded shape, in which the patch has an outer perimeter.

2. The ingestible pill according to claim 1, wherein the patch can inscribe a circle having a diameter of between 2 and 10 cm when the patch assumes the expanded shape and is unconstrained.

3. The ingestible pill according to claim 1, wherein each of the needles has a length of between 20 and 300 microns.

4. The ingestible pill according to claim 1, wherein the patch is configured such that the expanded shape is generally flat when the medication-delivery device is unconstrained.

5. The ingestible pill according to claim 1, wherein between 0% and 10% of the needles are coupled to the patch along the outer crease sides when the patch is disposed within the enteric coating.

6. The ingestible pill according to claim 1, wherein the ingestible pill is configured such that when the patch assumes the expanded shape upon dissolving of the enteric coating in a small intestine of a subject, the upper surface of the patch contacts an intestinal wall, thereby bringing the needles into contact with the intestinal wall.

7. The ingestible pill according to claim 6, wherein at least 50% of the needles are coupled to the upper surface of the patch along the inner crease sides when the patch is disposed within the enteric coating.

8. The ingestible pill according to claim 7, wherein at least 80% of the needles are coupled to the upper surface of the patch when the patch is disposed within the enteric coating.

9. The ingestible pill according to claim 6, wherein the patch is disposed within the enteric coating, folded such that when the patch assumes the expanded shape upon dissolving of the enteric coating in the small intestine, the upper face of the patch contacts the intestinal wall, thereby bringing the needles into contact with the intestinal wall.

10. The ingestible pill according to claim 1, wherein the medication-delivery device further comprises a medication, and wherein the needles are configured to deliver the medication.

11. The ingestible pill according to claim 10, wherein the needles are hollow and are configured to deliver the medication.

12. The ingestible pill according to claim 1, wherein the needles comprise a solid medication.

13. The ingestible pill according to claim 1, wherein the patch is disposed within the enteric coating, folded so as to define a plurality of creases.

14. The ingestible pill according to claim 13, wherein the patch is disposed within the enteric coating, folded first in half and then accordion-folded.

15. The ingestible pill according to claim 13, wherein the needles are not coupled to respective inner crease sides of a portion of the creases.

16. A method comprising:

receiving, by a subject, an ingestible pill, which includes (i) an enteric coating and (ii) a medication-delivery device, which includes (a) a patch having upper and lower surfaces that face in generally opposite directions, and needles, wherein the patch is disposed within the enteric coating, folded so as to define one or more creases, which define respective inner and outer crease sides, wherein at least one of the needles is coupled to the patch along the inner crease sides; and swallowing the ingestible pill by the subject, so that the coating dissolves in the small intestine and the patch assumes an expanded shape, in which the patch has an outer perimeter.

17. The method according to claim 16, wherein between 0% and 10% of the needles are coupled to the patch along the outer crease sides when the patch is disposed within the enteric coating.

18. The method according to claim 16, wherein the ingestible pill is configured such that when the patch assumes the expanded shape upon dissolving of the enteric coating in a small intestine of a subject, the upper surface of the patch contacts an intestinal wall, thereby bringing the needles into contact with the intestinal wall, and wherein at least 50% of the needles are coupled to the upper surface of the patch along the inner crease sides when the patch is disposed within the enteric coating.

19. The method according to claim 16, wherein the medication-delivery device further comprises a medication, and wherein the needles are configured to deliver the medication.

20. The method according to claim 16, wherein the needles comprise a solid medication.

21. The method according to claim 16, wherein the patch is disposed within the enteric coating, folded so as to define a plurality of creases, and wherein the needles are not coupled to respective inner crease sides of a portion of the creases.

* * * * *